(12) United States Patent
Fadli et al.

(10) Patent No.: US 7,887,601 B2
(45) Date of Patent: Feb. 15, 2011

(54) COMPOUNDS OF AZOMETHINE TYPE COMPRISING A CATIONIC PYRAZOLOPYRIDINE UNIT, FOR DYEING KERATIN FIBRES

(75) Inventors: Aziz Fadli, Chelles (FR); Stéphane Blais, Palaiseau (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/769,162

(22) Filed: Apr. 28, 2010

(65) Prior Publication Data

US 2010/0275390 A1 Nov. 4, 2010

Related U.S. Application Data

(60) Provisional application No. 61/177,746, filed on May 13, 2009.

(30) Foreign Application Priority Data

Apr. 30, 2009 (FR) .................................. 09 52898

(51) Int. Cl.
*A61Q 5/10* (2006.01)
*C07D 231/44* (2006.01)

(52) U.S. Cl. .................. 8/405; 8/406; 8/426; 8/435; 8/570; 8/572; 8/573; 8/576; 548/367.7

(58) Field of Classification Search .............. 8/405, 8/406, 426, 435, 570, 572, 573, 576; 548/367.7
See application file for complete search history.

(56) References Cited

U.S. PATENT DOCUMENTS

| 6,730,789 | B1 | 5/2004 | Birault et al. |
|---|---|---|---|
| 7,578,855 | B2 | 8/2009 | Fadli |
| 7,578,856 | B2 | 8/2009 | Saunier |
| 7,582,123 | B2 | 9/2009 | Fadli et al. |
| 7,648,536 | B2 | 1/2010 | Saunier et al. |
| 2009/0044348 | A1* | 2/2009 | Fadli et al. .................... 8/405 |

FOREIGN PATENT DOCUMENTS

| FR | 2 801 308 A1 | 5/2001 |
|---|---|---|
| FR | 2 893 027 A1 | 5/2007 |
| FR | 2 915 879 A1 | 11/2008 |
| FR | 2 915 880 A1 | 11/2008 |
| FR | 2 915 881 A1 | 11/2008 |
| FR | 2 915 882 A1 | 11/2008 |
| FR | 2 915 883 A1 | 11/2008 |
| FR | 2 915 884 A1 | 11/2008 |
| FR | 2 915 885 A1 | 11/2008 |
| FR | 2 915 886 A1 | 11/2008 |
| FR | 2 915 887 A1 | 11/2008 |
| FR | 2 917 737 A1 | 12/2008 |
| FR | 2 920 090 A1 | 2/2009 |
| FR | 2 920 091 A1 | 2/2009 |

OTHER PUBLICATIONS

STIC Search Report dated Sep. 27, 2010.*
French Search Report for FR 0952898, dated Nov. 16, 2009.
English language abstract of FR 2 915 881 A1, Nov. 14, 2008.
English language abstract of FR 2 915 882 A1, Nov. 14, 2008.
English language abstract of FR 2 915 883 A1, Nov. 14, 2008.
English language abstract of FR 2 915 884 A1, Nov. 14, 2008.
English language abstract of FR 2 915 885 A1, Nov. 14, 2008.
English language abstract of FR 2 915 886 A1, Nov. 14, 2008.
English language abstract of FR 2 915 887 A1, Nov. 14, 2008.
English language abstract of FR 2 920 090 A1, Feb. 27, 2009.
English language abstract of FR 2 920 091 A1, Feb. 27, 2009.

* cited by examiner

*Primary Examiner*—Eisa B Elhilo
(74) *Attorney, Agent, or Firm*—Finnegan, Henderson, Farabow, Garrett & Dunner, LLP

(57) ABSTRACT

Disclosed herein is at least one compound chosen from compounds of leuco type of formula (I), dyes of azomethine type comprising a pyrazolopyridine unit of formula (II) corresponding to the compounds of formula (I), mesomeric forms, isomeric and tautomeric forms thereof, acid-addition salts thereof and solvates thereof:

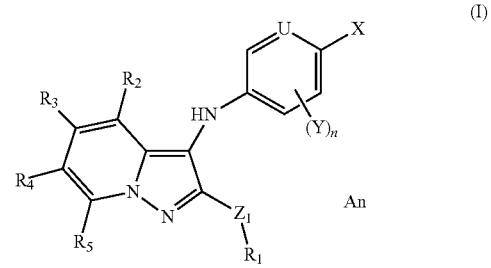

(I)

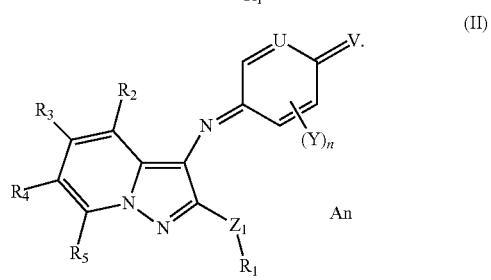

(II)

18 Claims, No Drawings

COMPOUNDS OF AZOMETHINE TYPE COMPRISING A CATIONIC PYRAZOLOPYRIDINE UNIT, FOR DYEING KERATIN FIBRES

This application claims benefit of U.S. Provisional Application No. 61/177,746, filed May 13, 2009. This application also claims benefit of priority under 35 U.S.C. §119 to French Patent Application No. 0952898, filed Apr. 30, 2009.

Disclosed herein are compounds of azomethine type comprising a cationic pyrazolopyridine unit and a composition thereof for dyeing keratin fibers, and for example human keratin fibers such as the hair.

It may be known practice to dye keratin fibers with dye compositions comprising direct dyes. These compounds are colored and coloring molecules that can have affinity for the fibers. It may be known practice, for example, to use direct dyes of the nitrobenzene type, anthraquinone dyes, nitropyridine dyes, and dyes of the azo, xanthine, acridine, azine or triarylmethane type.

These dyes can be applied to the fibers, optionally in the presence of an oxidizing agent, if it is desired to obtain a simultaneous lightening effect on the fibers. Once the leave-on time has passed, the fibers can be rinsed, and optionally washed and dried.

The colorations resulting from the use of direct dyes can be colorations that can be often chromatic, but may be, however, temporary or semi-permanent since the nature of the interactions that bind the direct dyes to the keratin fiber, and their desorption from the surface and/or the core of the fiber, can be responsible for their poor dyeing power and their poor relative fastness with respect to washing or perspiration. These direct dyes can be also for example light-sensitive since the resistance of the chromophore to photochemical attack can be poor, which may lead to the fading of the hair coloration over time. The sensitivity of these dyes to light may depend on their distribution uniformly or as aggregates in and/or on the keratin fiber.

To obtain the similar result, it can be possible to use the uncolored, reduced form of these dyes, also called the leuco form, and to apply it to the fibers in the presence of at least one oxidizing agent so as to generate the colored and coloring oxidized form. The coloration obtained may then be eliminated and then reformed rapidly by passing from one form to the other.

Thus, it may be known from French patent application FR 2 917 737 to use compounds of azomethine type comprising a pyrazolinone unit and reduced forms thereof so as to obtain a keratin fiber coloration that can be eliminated and then reformed easily.

Provided herein thus are novel direct dyes for reversibly dyeing keratin fibers, while at the same time being capable of giving good dyeing properties.

For example, disclosed herein are direct dyes for obtaining a strong, chromatic, aesthetic, sparingly selective coloration in varied shades, which can withstand at least one of the various attacking factors to which the hair may be subjected, such as shampoos, light, sweat and permanent reshaping, and which can be removed easily.

Provided herein is at least one compound chosen from the leuco form compounds of formula (I), dyes of azomethine type comprising a pyrazolopyridine unit of formula (II), mesomeric forms, isomeric and tautomeric forms thereof, and also acid-addition salts thereof and solvates thereof:

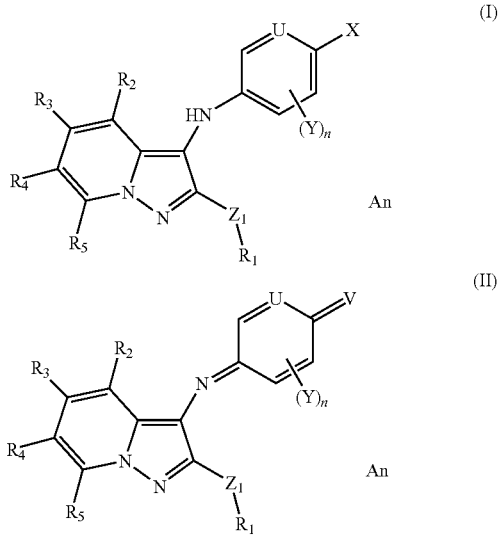

in which:

Z$_1$ represents:
a single covalent bond;
a divalent radical chosen from:
    an oxygen atom; and
    a NR$_6$(R$_7$)p, with p=0 or 1;
when p is equal to 0, R$_6$ represents a hydrogen atom or a C$_1$-C$_6$ alkyl, or R$_6$ with R$_1$ form, together with the nitrogen atom to which they are attached, a substituted or unsubstituted, saturated or unsaturated, aromatic or non-aromatic 5- to 8-membered heterocycle optionally comprising at least one additional radical chosen from N, O, S, SO$_2$ and —CO—, wherein the heterocycle can be cationic and/or substituted with at least one cationic or non-cationic radical;
when p is equal to 1, NR$_6$R$_7$ is a cationic radical in which R$_6$ and R$_7$ independently represent an alkyl radical;
Z$_1$ can also represent a divalent radical —S—, —SO—, or —SO$_2$— when R$_1$ is a methyl;
R$_1$ represents:
a hydrogen;
an optionally substituted C$_1$-C$_{10}$ alkyl, optionally interrupted with at least one radical chosen from O, N, Si, S, SO and SO$_2$;
a C$_1$-C$_{10}$ alkyl substituted and/or interrupted with a cationic radical;
a halogen;
a radical SO$_3$H; or
a substituted or unsubstituted, saturated, unsaturated or aromatic 5- to 8-membered ring, optionally comprising at least one radical chosen from N, O, S, SO$_2$ and —CO—, the ring can be cationic and/or substituted with a cationic radical;
when Z$_1$ represents a covalent bond, R$_1$ can represent:
an optionally substituted C$_1$-C$_6$ alkylcarbonyl; or
a radical —O—CO—R, —CO—O—R, —NR—CO—R' or —CO—NRR' in which R and R' independently represent a hydrogen atom or an optionally substituted C$_1$-C$_6$ alkyl;

$R_2$, $R_3$, $R_4$ and $R_5$, which may be identical or different, represent:
- a hydrogen atom;
- a hydroxyl;
- a $C_1$-$C_6$ alkoxy;
- a $C_1$-$C_6$ alkylthio;
- an amino;
- a monoalkylamino;
- a $C_1$-$C_6$ dialkylamino in which the alkyl can form, with the nitrogen atom to which they are attached, a saturated or unsaturated, aromatic or non-aromatic 5- to 8-membered heterocycle optionally comprising at least one additional radical chosen from N, O, S, $SO_2$ and CO, the heterocycle can be cationic and/or substituted with a cationic radical;
- an optionally substituted $C_1$-$C_6$ alkylcarbonyl;
- a —O—CO—R, —CO—O—R, —NR—CO—R' or —CO—NRR' in which R and R' independently represent a hydrogen atom or an optionally substituted $C_1$-$C_6$ alkyl;
- a halogen;
- a $NHSO_3H$;
- an optionally substituted $C_1$-$C_4$ alkyl;
- a saturated, unsaturated or aromatic, optionally substituted carbon-based ring; or
- two adjacent $R_2$, $R_3$, $R_4$ and $R_5$ may form, together with the carbons they are attached, a saturated or unsaturated 5- or 6-membered ring;

An represents at least one anion that ensures the electronegativity of the compounds of formulae (I) and (II);
provided that at least one of the groups $Z_1$ and $R_1$ represents a cationic radical;
n is an integer ranging from 0 to 3;
U represents CR or N;
R represents:
- a hydrogen atom;
- a $C_1$-$C_4$ alkyl optionally substituted with a hydroxyl;
- a $C_1$-$C_4$ alkoxy optionally substituted with a hydroxyl; or
- a (di)($C_1$-$C_4$)alkylamino in which the alkyl part is optionally substituted with a hydroxyl;

X represents:
- a hydroxyl; or
- a group $NR'_1R''_1$, wherein $R'_1$ and $R''_1$ are chosen independently from a hydrogen atom; a $C_1$-$C_6$ alkyl optionally substituted with at least one radical chosen from hydroxyl, ($C_1$-$C_2$)alkoxy, amino, and (di)($C_1$-$C_2$)alkylamino; and a phenyl radical optionally substituted with at least one radical chosen from hydroxyl, amino and ($C_1$-$C_2$)alkoxy;

when $R'_1$ and $R''_1$ are other than a hydrogen, $R'_1$ and $R''_1$ can form, together with the nitrogen atom to which they are attached, a saturated or unsaturated 5- to 7-membered heterocycle optionally comprising at least one additional heteroatom chosen from an oxygen and nitrogen atom, and optionally substituted with at least one radical chosen from halogen, amino, (di)($C_1$-$C_4$)alkylamino, hydroxyl, carboxyl, carboxamido, ($C_1$-$C_2$)alkoxy and $C_1$-$C_4$ alkyl, optionally substituted with at least one radical chosen from hydroxyl, amino, (di)alkylamino, alkoxy, carboxyl and sulfonyl radical;

when X represents a group $NHR'_1$ and when U represents a group CR in which R denotes an alkoxy, X and U may form a 6-membered ring of morpholine type, optionally substituted with at least one $C_1$-$C_4$ alkyl;

V represents:
- an oxygen atom; or
- a group $NR'_1$, wherein $R'_1$ is chosen from a hydrogen atom; a $C_1$-$C_6$ alkyl optionally substituted with at least one radical chosen from hydroxyl, ($C_1$-$C_2$)alkoxy, and amino and (di)($C_1$-$C_2$)alkylamino; and a phenyl radical optionally substituted with at least one radical chosen from hydroxyl, amino and ($C_1$-$C_2$)alkoxy;

when V represents a group $NR'_1$ and when U represents a group CR in which R denotes an alkoxy, V and U can form a 6-membered ring of morpholine type, optionally substituted with at least one $C_1$-$C_4$ alkyl;

Y, which may be identical or different, represent:
- a hydroxyl;
- a $C_1$-$C_4$ alkyl;
- a $C_1$-$C_4$ hydroxyalkyl;
- a halogen;
- an oxygen atom substituted with a radical chosen from a $C_1$-$C_4$ alkyl, an aryl radical and a heteroaryl radical, optionally substituted with at least one hydroxyl; or
- a group $NR'_2R'_3$,
  $R'_2$ and $R'_3$, which may be identical or different, are chosen from:
  - a hydrogen atom;
  - a $C_1$-$C_4$ alkylcarbonyl optionally substituted with a quaternary ammonium group, or with a cationic or non-cationic nitrogenous heterocycle optionally substituted with at least one $C_1$-$C_4$ alkyl;
  - an aminocarbonyl;
  - a $C_1$-$C_6$ alkyl optionally substituted with at least one radical chosen from hydroxyl, ($C_1$-$C_2$)alkoxy, amino and (di)($C_1$-$C_2$)alkylamino; and
  - a phenyl optionally substituted with at least one radical chosen from hydroxyl, amino and ($C_1$-$C_2$)alkoxy; or
  $R'_2$ and $R'_3$ can form, together with the nitrogen atom to which they are attached, a saturated or unsaturated, 5- to 7-membered heterocycle optionally comprising at least one additional heteroatom chosen from an oxygen and nitrogen atom, and optionally substituted with at least one radical chosen from a halogen, amino, (di)($C_1$-$C_4$)alkylamino, hydroxyl, carboxyl, (di)alkylcarboxamido, ($C_1$-$C_2$)alkoxy and $C_1$-$C_4$, optionally substituted with at least one radical chosen from hydroxyl, amino, (di)alkylamino, alkoxy, carboxyl and sulfonyl; or
- two radicals Y borne by two adjacent carbon atoms may form, together with the carbon atoms to which they are attached, a saturated or unsaturated, aromatic or non-aromatic, 5- to 6-membered cyclic or heterocyclic optionally substituted with at least one $C_1$-$C_4$ alkyl.

Provided herein is also a composition for dyeing keratin fibers, comprising, in a suitable dyeing medium, at least one compound chosen from the leuco form compounds of formula (I), the dyes of azomethine type comprising a pyrazolopyridine unit of formula (II), the mesomeric forms, isomeric and tautomeric forms thereof, acid-addition salts thereof and the solvates thereof.

Provided herein is also a method for dyeing keratin fibers comprising applying to the keratin fibers at least one composition comprising at least one compound chosen from the leuco form compounds of formula (I), the dyes of azomethine type comprising a pyrazolopyridine unit of formula (II), the mesomeric forms, isomeric and tautomeric forms thereof, acid-addition salts thereof and the solvates thereof.

Provided herein is also a multi-compartment device for performing the method in accordance with the disclosure.
fiberUnless otherwise indicated, the limits of the ranges of values are included in these ranges.

Unless otherwise mentioned, the term "alkyl radical" means linear or branched alkyl radicals, which may be substituted or unsubstituted. Unless specifically listed, they may be substituted with any conventional substituent in the field of dyeing that does not change the dyeing properties of the compounds of formula (I) and/or (II).

An alkoxy is an alkyl-O— radical, the alkyl radical being as defined previously.

A (di)alkylamino is an amino radical that may be substituted with one or two alkyl radicals.

A (di)alkylcarboxamido is a carboxamido radical that may be substituted with one or two alkyl radicals.

As examples of substituents on these alkyls, mention may be made of the following substituents: halo; hydroxyl; alkoxy; amino; thio, alkylthio, $C_1$-$C_6$ alkylamino; $C_1$-$C_6$ dialkylamino in which the alkyl may form, with the nitrogen atom to which they are attached, a saturated or unsaturated, aromatic or non-aromatic, cationic or non-cationic 5- to 8-membered heterocycle optionally comprising at least one additional radical chosen from N, O, S, $SO_2$ and CO, the heterocycle is optionally substituted; ($C_1$-$C_6$)alkylcarbonyl; —O—CO—R; —CO—O—R; NR—CO—R' or —CO—NRR' in which R and R' are as defined previously, a quaternary ammonium radical as defined previously.

This applies to the alkyl present in any of the radicals defined in formulae (I) and (II), for example the alkyl in alkoxy (alkyl-O—) or alkylthio.

As examples of the substituents on the rings or heterocycles, mention may be made of alkyl, substituted alkyl, hydroxyl, alkoxy, amino, alkylamino and dialkylamino.

The term "cationic radical present in the compounds of formulae (I) and (II)" means any linear or branched radical comprising a quaternary ammonium, this quaternary ammonium can be of the type —$N^+R_{17}R_{18}R_{19}$, wherein $R_{17}$, $R_{18}$ and $R_{19}$, which may be identical or different, represent a $C_1$-$C_6$ alkyl optionally substituted with a hydroxyl.

The term "cationic ring" or "cationic heterocycle" means a ring or a heterocycle comprising a quaternary ammonium.

As examples of radicals of the type —$N^+R_{17}R_{18}R_{19}$, mention may be made of trimethylammonium, triethylammonium, dimethylethylammonium, diethylmethylammonium, diisopropylmethylammonium, diethylpropylammonium, hydroxyethyldiethylammonium, bis(β-hydroxyethyl)methylammonium and tris(β-hydroxyethyl)ammonium.

Examples of cationic heterocycles that may be mentioned include imidazoliums, pyridiniums, piperaziniums, pyrrolidiniums, morpholiniums, pyrimidiniums, thiazoliums, benzimidazoliums, benzothiazoliums, oxazoliums, benzotriazoliums, pyrazoliums, triazoliums and benzoxazoliums.

According to at least one embodiment of the disclosure, $Z_1$ represents a single covalent bond, a radical —O—, a radical —$NR_6$— wherein $R_6$ represents a hydrogen atom or an alkyl, or $R_6$ forms with $R_1$ a heterocycle that is cationic and/or substituted with a cationic radical.

When $R_6$ forms with $R_1$ a heterocycle, this heterocycle can be a cationic heterocycle or a heterocycle substituted with a cationic radical. Examples that may be mentioned include imidazoles substituted with a quaternary ammonium or imidazoliums, piperazines substituted with a quaternary ammonium or piperaziniums, pyrrolidines substituted with a quaternary ammonium or pyrrolidiniums, and diazepans substituted with a quaternary ammonium or diazepaniums.

For example, $Z_1$ represents a single covalent bond, a radical —O— or a radical —NH—.

According to at least one embodiment, $R_1$ represents a hydrogen atom, an alkyl that may be interrupted or substituted with a cationic radical, such as alkylammonium, hydroxyalkylammonium, imidazolium, piperazinium, pyrrolidinium or diazepanium, imidazolyl substituted with a cationic radical, piperazinyl substituted with a cationic radical, pyrrolidinyl substituted with a cationic radical, or pyridinyl substituted with a cationic radical.

For example, $R_1$ represents a hydrogen atom, a piperazinium, a $C_1$-$C_4$ alkyl substituted with a cationic radical chosen from a tri($C_1$-$C_4$)alkylammonium, such as trimethylammonium, an imidazolium or a pyrrolidinium.

$R_2$, $R_3$, $R_4$ and $R_5$, independently, may be a hydrogen atom or a $C_1$-$C_4$ alkyl that may be substituted with at least one radical chosen from methyl, ethyl, hydroxyethyl, aminoethyl, propyl and butyl. According to one embodiment, $R_2$, $R_3$, $R_4$ and $R_5$ independently represent a hydrogen atom or a $C_1$-$C_4$ alkyl.

According to at least one embodiment, U represents CR or N, and R represents a hydrogen atom, a $C_1$-$C_4$ alkyl, a $C_1$-$C_4$ alkoxy optionally substituted with a hydroxyl, a (di)($C_1$-$C_4$) alkylamino in which the alkyl is optionally substituted with at least one hydroxyl.

For example, U represents CR or N, and R represents a hydrogen atom, a methyl, a methoxy, a 2-hydroxyethyloxy, a methylamino, a dimethylamino or hydroxyethylamino or a dihydroxyethylamino or methyl(hydroxyethyl)amino.

For further example, U represents CR or N, and R represents a hydrogen atom, a methyl, a hydroxyethyloxy or a chlorine atom.

According to at least one embodiment of the disclosure, X represents a hydroxyl; the group $NR'_1R''_1$ with $R'_1$ and $R''_1$ chosen independently from a hydrogen atom and a $C_1$-$C_6$ alkyl optionally substituted with at least one hydroxyl radical.

For example, X represents a hydroxyl; a group $NR'_1R''_1$ with $R'_1$ and $R''_1$ independently chosen from a hydrogen atom; a methyl; and a 2-hydroxyethyl.

According to at least one embodiment, when $R'_1$ and $R''_1$ form a heterocycle, this heterocycle may be chosen from pyrrolidine, piperidine, homopiperidine, piperazine, homopiperazine and morpholine, optionally substituted with at least one radical chosen from a halogen atom and amino (di)($C_1$-$C_4$)alkylamino, hydroxyl, carboxyl, (di)alkylcarboxamido, ($C_1$-$C_2$)alkoxy and $C_1$-$C_4$ alkyl, optionally substituted with at least one radical chosen from hydroxyl, amino, (di)alkylamino, alkoxy, carboxyl and sulfonyl. By way of example, these heterocycles can be chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(2-hydroxyethyl)-aminopyrrolidine, piperidine, 2,6-dimethylpiperidine, 2-carboxypiperidine, 2-carboxamido-piperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, carboxyhomopiperidine, 2-carboxamidohomopiperidine, homopiperazine, N-methyl-homopiperazine, N-(2-hydroxyethyl)homopiperazine and morpholine.

Further for example, these heterocycles are chosen from pyrrolidine, 3-hydroxypyrrolidine, 3-aminopyrrolidine, 3-dimethylaminopyrrolidine, pyrrolidine-2-carboxylic acid, 3-hydroxypyrrolidine-2-carboxylic acid, piperidine, 4-hydroxypiperidine, homopiperidine, homopiperazine, N-methylhomopiperazine, N-(2-hydroxyethyl)homopiperazine and morpholine.

According to one embodiment, $R_1$ and $R''_1$ form, together with the nitrogen atom to which they are attached, a 5-membered ring such as pyrrolidine, 3-hydroxypyrrolidine, 3-aminopyrrolidine or 3-dimethylaminopyrrolidine.

According to one embodiment of the disclosure, V represents:
an oxygen atom; or
a group $NR'_1$ in which $R'_1$ represents a hydrogen atom or a $C_1$-$C_6$ alkyl optionally substituted with at least one hydroxyl.

For example, V represents:
an oxygen atom; or
a group $NR'_1$ in which $R'_1$ represents a hydrogen atom or a $C_1$-$C_6$ alkyl optionally substituted with at least one hydroxyl.

Further for example, V can represent a hydrogen atom or an NH group.

According to at least one embodiment of the disclosure, X and U, or, respectively, V and U, form a 6-membered ring such as morpholine, optionally substituted with at least one $C_1$-$C_4$ alkyl, which is for example unsubstituted.

According to at least one embodiment of the disclosure, Y, which may be identical or different, represent a hydroxyl; a $C_1$-$C_4$ alkyl; a halogen; an oxygen substituted with a $C_1$-$C_4$ alkyl which may be substituted with at least one hydroxyl; or group $NR'_2R'_3$;

$R'_2$ and $R'_3$, which may be identical or different, may be chosen from a hydrogen atom; a $C_1$-$C_4$ alkylcarbonyl; an aminocarbonyl; and a $C_1$-$C_6$ alkyl optionally substituted with at least one hydroxyl;

$R'_2$ and $R'_3$ may form, together with the nitrogen atom to which they are attached, a saturated 5- to 7-membered heterocycle.

According to at least one embodiment, these heterocycles are chosen from pyrrolidine, piperidine, homopiperidine, piperazine, homopiperazine and morpholine, which are optionally substituted with at least one radical chosen from a halogen, amino, (di)($C_1$-$C_4$)alkylamino, hydroxyl, carboxyl, (di)alkylcarboxamido, ($C_1$-$C_2$)alkoxy and $C_1$-$C_4$ alkyl, optionally substituted with at least one radical chosen from hydroxyl, amino, (di)alkylamino, alkoxy, carboxyl and sulfonyl.

Two radicals Y borne by two adjacent carbon atoms may form, together with the carbon atoms to which they are attached, a saturated or unsaturated, aromatic or non-aromatic 5- or 6-membered cyclic or heterocyclic group.

For example, Y, which may be identical or different, represent a hydroxyl; a $C_1$-$C_4$ alkyl; a halogen, such as a chlorine atom; or a group $NR'_2R'_3$;
wherein $R'_2$ and $R'_3$, which may be identical or different, are chosen from a hydrogen atom and a $C_1$-$C_4$ alkyl optionally substituted with one or two hydroxyl radicals.

Further for example, Y, which may be identical or different, represent a hydroxyl; a methyl; a chlorine; a 2-hydroxyethyloxy; an amino; or a (2-hydroxyethyl)amino.

The term "addition salts" means the salts of physiologically acceptable organic or mineral acids and the compounds of formula (I) and/or (II).

The leuco form compounds of formula (I), and the dyes of azomethine type comprising a pyrazolopyridine unit of formula (II), may be optionally salified with strong mineral acids, for instance HCl, HBr, HI, $H_2SO_4$, $H_3PO_4$, or organic acids, for instance acetic acid, lactic acid, tartaric acid, citric acid or succinic acid, benzenesulfonic acid, para-toluenesulfonic acid, formic acid or methanesulfonic acid.

As disclosed, the term "derivative of formula (I) and/or (II)" means any mesomeric form or isomer thereof.

They may also be in the form of solvates, for example a hydrate or a solvate of a linear or branched alcohol such as ethanol or isopropanol.

The present disclosure makes it possible for example rapidly to obtain chromatic colorations that can be resistant to at least one of the various attacking factors to which the hair may be subjected, and for example to shampoos and light, these colorations can be removed and then reformed just as quickly.

The leuco form compounds of formula (I) are colorless or weakly colored, and the corresponding azomethine derivatives comprising a pyrazolopyridine unit of formula (II) are colored and coloring species. It is possible to modify the structure of the compounds of formula (I) to obtain the compounds of formula (II) by adding at least one oxidizing agent, and, conversely, it is possible to modify the structure of the compounds of formula (II) to obtain the compounds of formula (I) by adding at least one reducing agent. This structure modification may be facilitated by modifying the pH and/or the temperature. Formation of the compounds of formula (I) is thus promoted by acidic pH and/or reducing the temperature, and formation of the compounds of formula (II) is promoted by basic pH and/or raising the temperature. Such behavior makes it possible for example to readily modify the coloration of keratin fibers.

According to at least one embodiment, the compounds are chosen from compounds of formulae (I) and (II) in which $Z_1$ represents a radical —O—, a radical —NH— or a single covalent bond;

$R_1$ represents a piperazinium, or a $C_1$-$C_4$ alkyl substituted with a cationic radical chosen from a tri($C_1$-$C_4$)alkyl ammonium, such as trimethylammonium, an imidazolium or a pyrrolidinium;

$R_3$, $R_4$ and $R_5$ independently represent a hydrogen atom or a $C_1$-$C_4$ alkyl;

n is an integer ranging from 0 to 3;

U represents CR or N, and R represents a hydrogen atom, a methyl, a methoxy, a 2-hydroxyethyloxy, a methylamino, a dimethylamino, a hydroxyethylamino, a dihydroxyethylamino, or a methyl(hydroxyethyl)amino. For example, U represents CR or N, and R represents a hydrogen atom, a methyl, a 2-hydroxyethyloxy I or a chlorine;

Y, which may be identical or different, represent a hydroxyl; a $C_1$-$C_4$ alkyl; a halogen, such as a chlorine; a group $NR'_2R'_3$ wherein $R'_2$ and $R'_3$, which may be identical or different, are chosen from a hydrogen atom and a $C_1$-$C_4$ alkyl optionally substituted with at least one hydroxyl; For example, Y, which may be identical or different, represent a hydroxyl; a methyl; a chlorine; a 2-hydroxyethyloxy; an amino; or a (2-hydroxyethyl) amino;

X represents a hydroxyl; a group $NR'_1R''_1$ wherein $R'1$ and $R''_1$ are independently chosen from a hydrogen atom; a methyl and a 2-hydroxyethyl, or $R_1$ and $R''_1$ form, together with the nitrogen atom to which they are attached, a 5-membered ring such as pyrrolidine, 3-hydroxypyrrolidine, 3-aminopyrrolidine or 3-dimethylaminopyrrolidine; or X and U, or, respectively, V and U, form a 6-membered ring of morpholine type, optionally substituted with at least one $C_1$-$C_4$ alkyl, which is for example unsubstituted.

As examples of dyes of azomethine type comprising a pyrazolopyridine unit of formula (II), mention may be made of the compounds presented below:

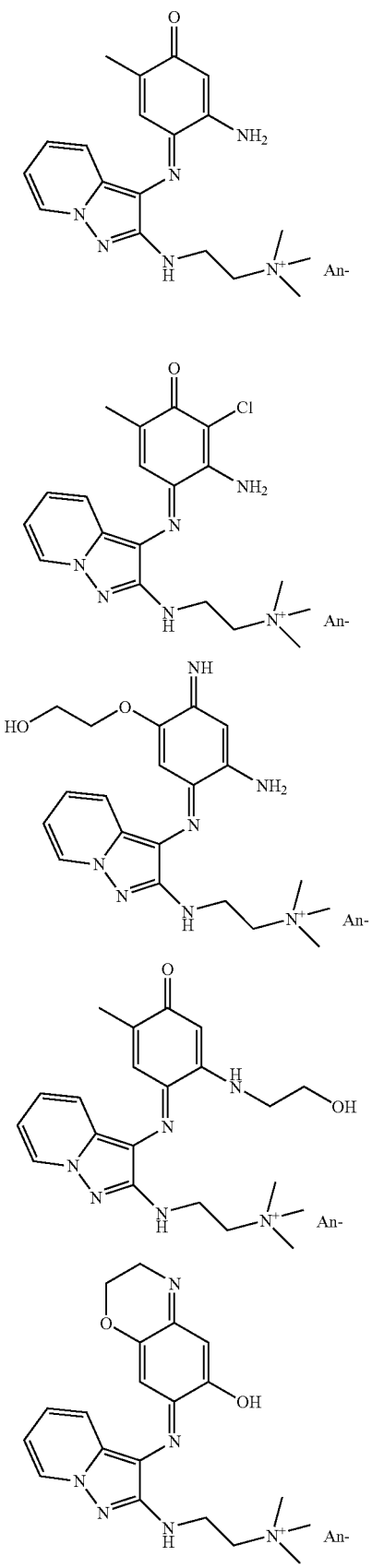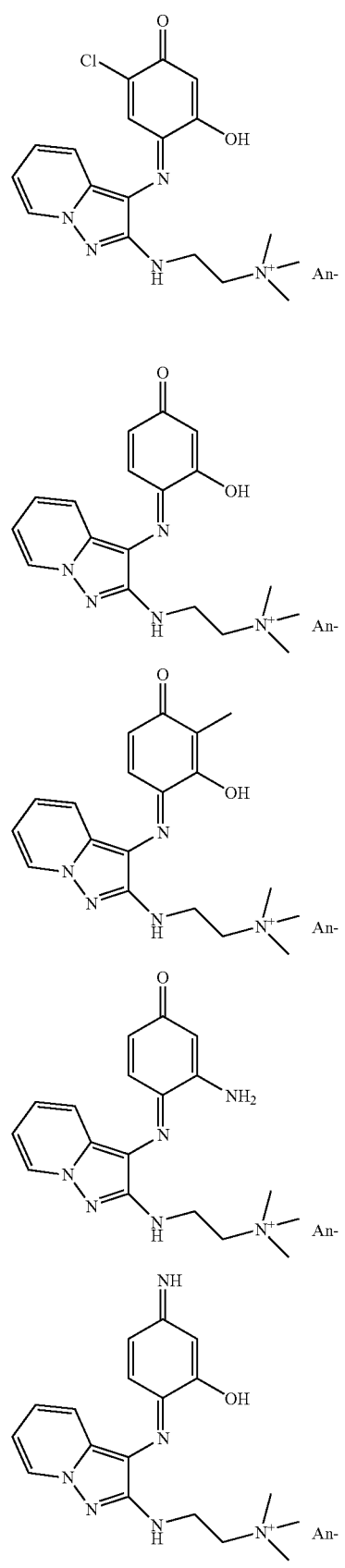

-continued
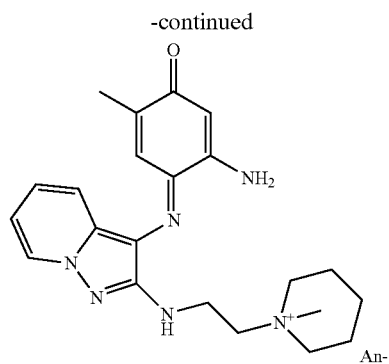
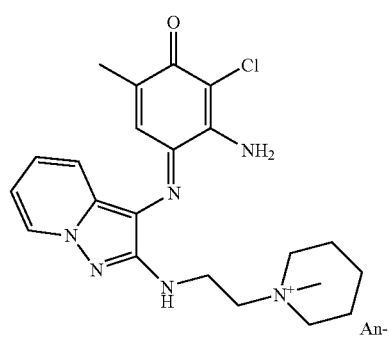
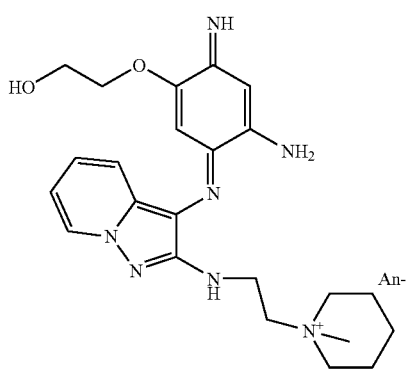
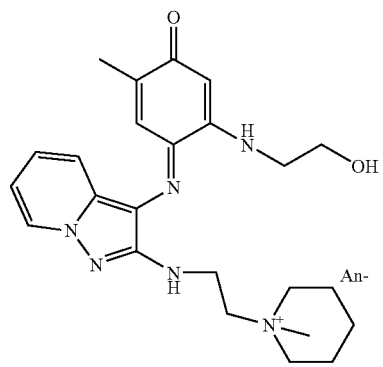
-continued
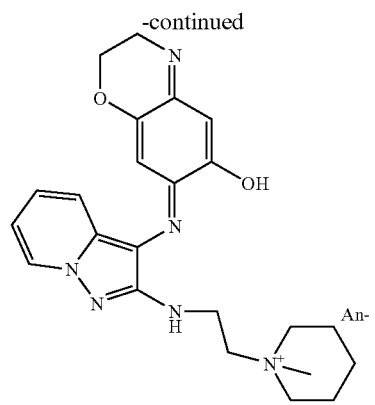
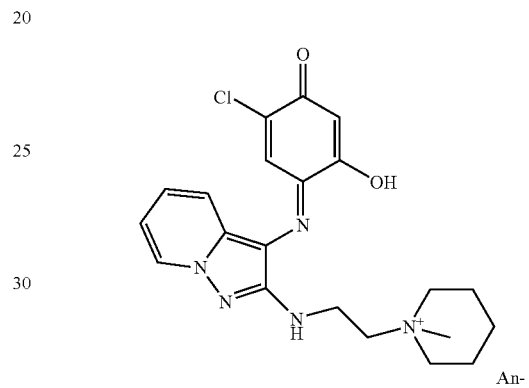
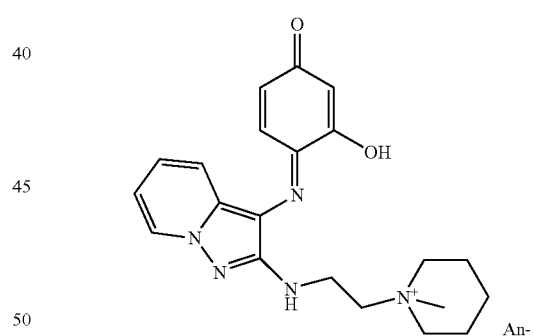
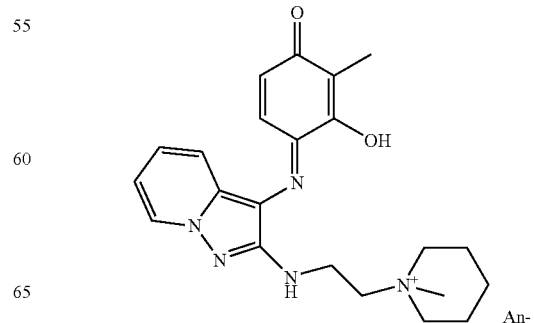

13
-continued
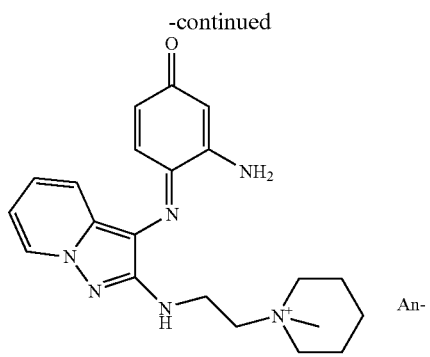
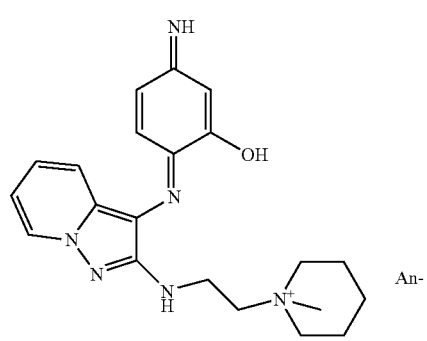
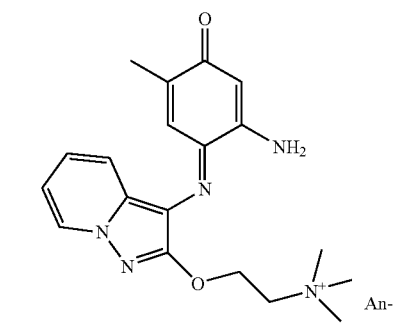
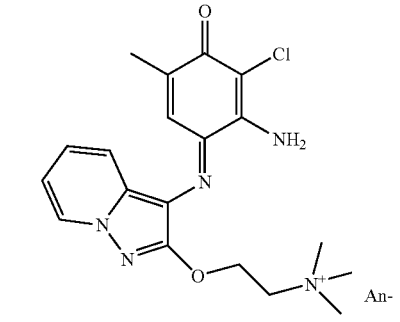
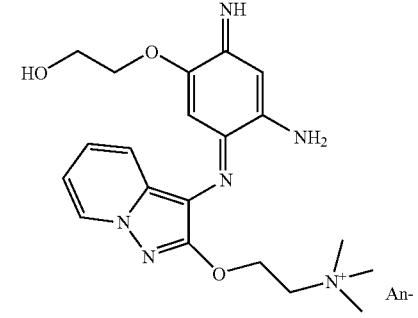
14
-continued
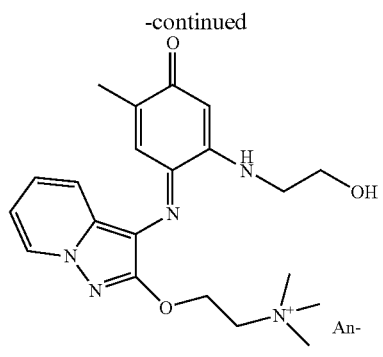
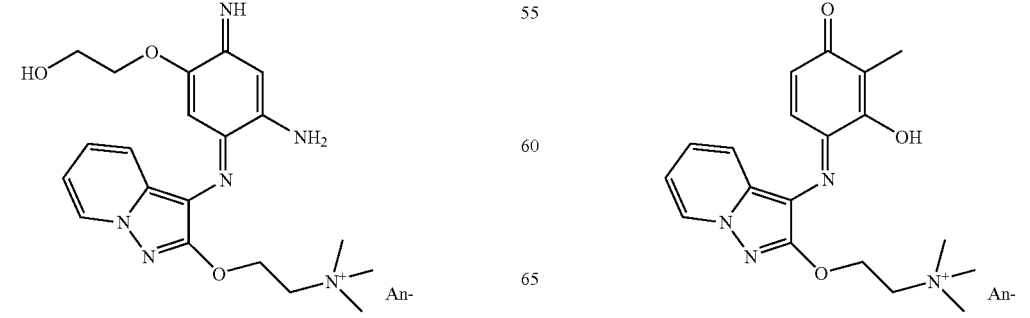

-continued
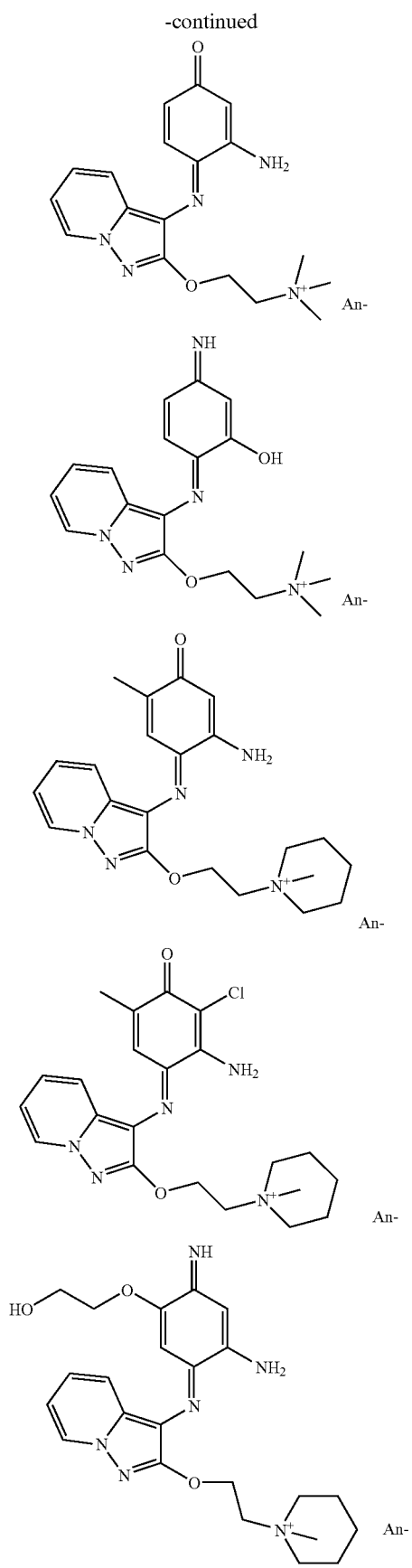
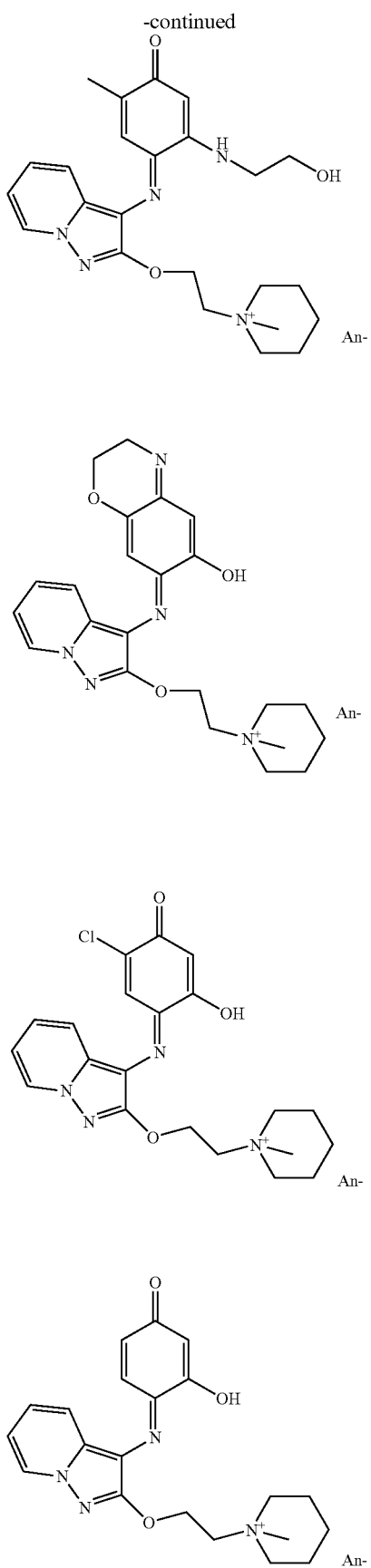

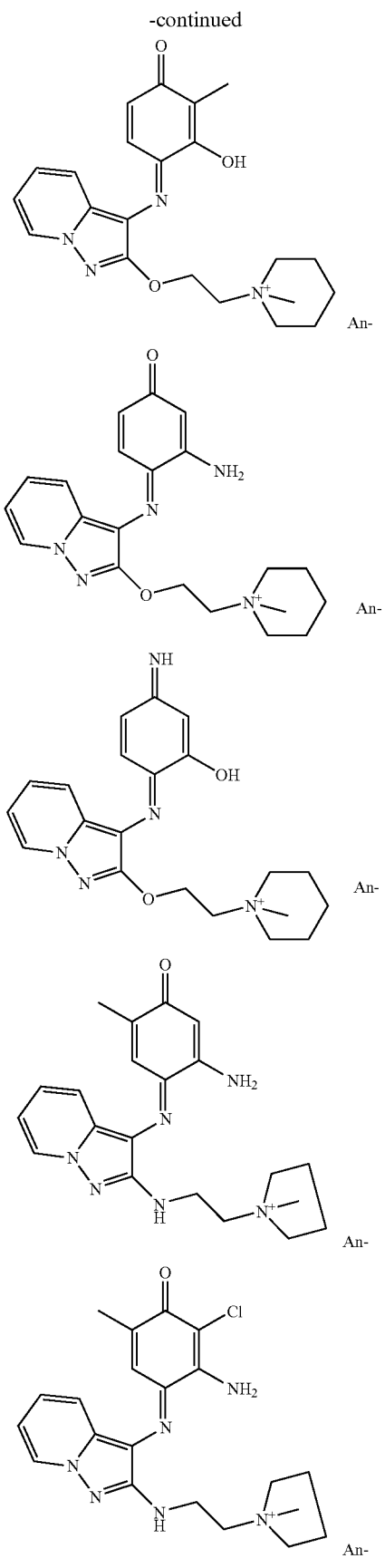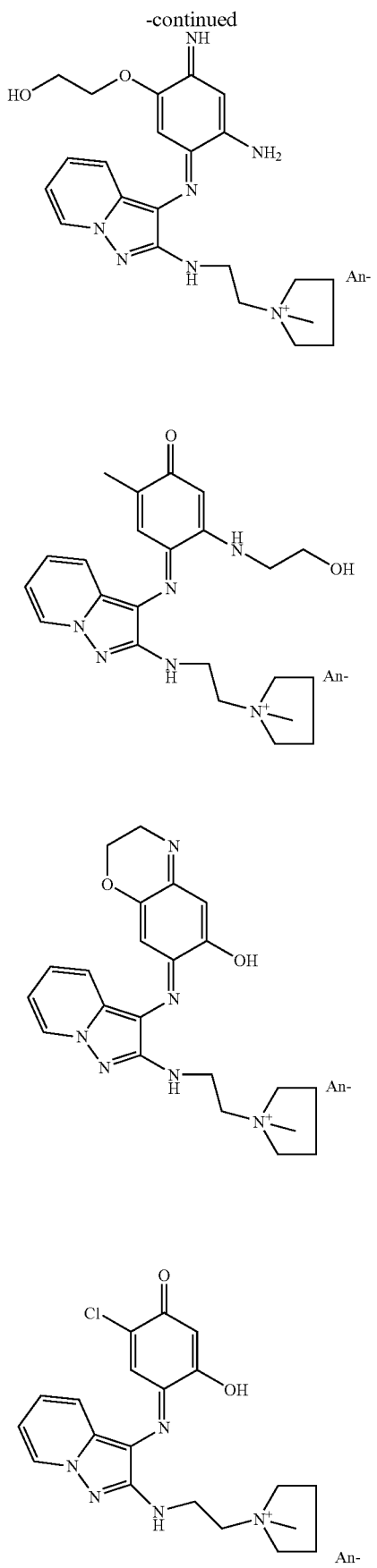

-continued
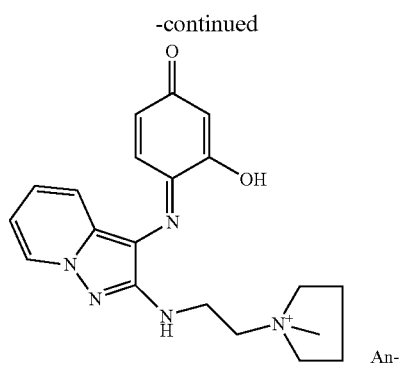
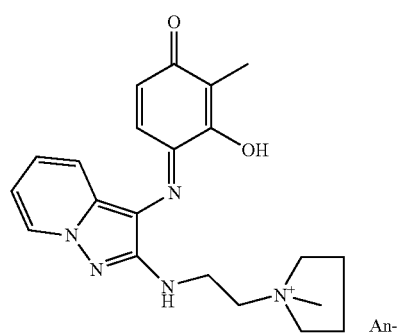
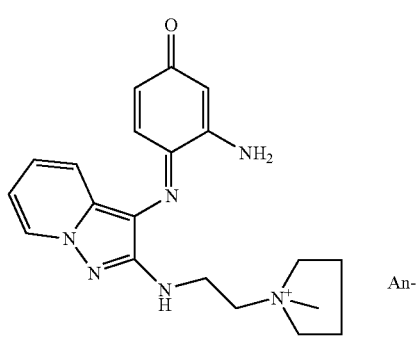
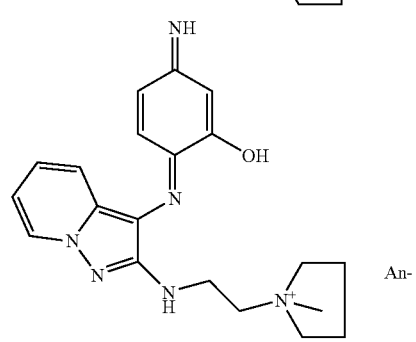
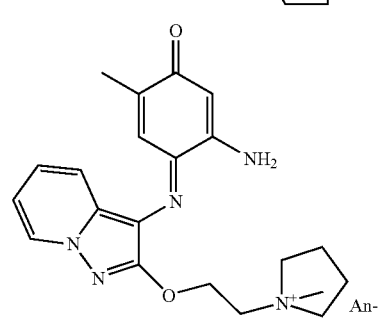
-continued
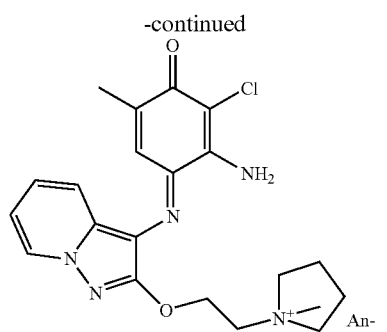
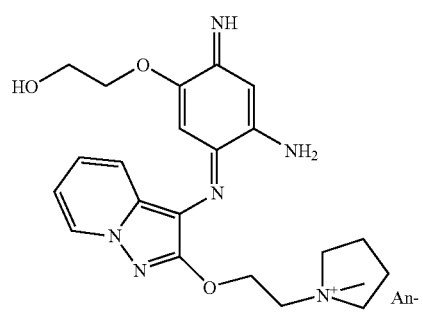
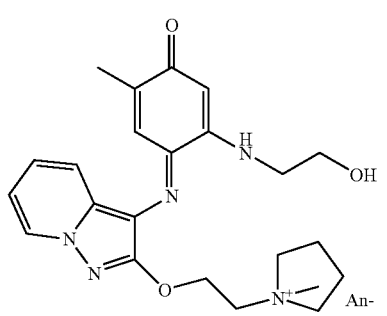
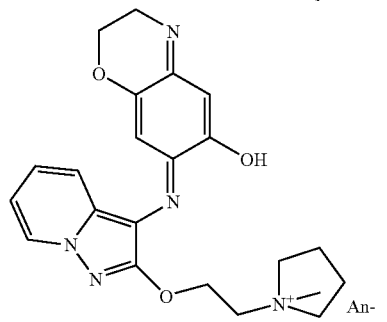
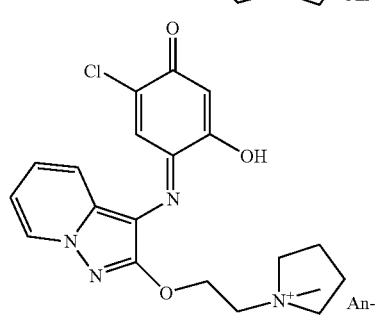

-continued
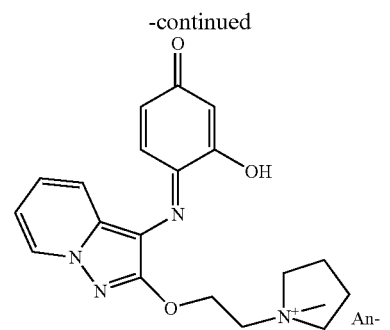
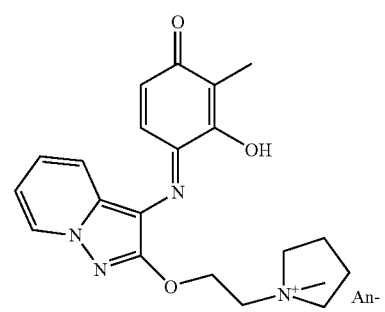
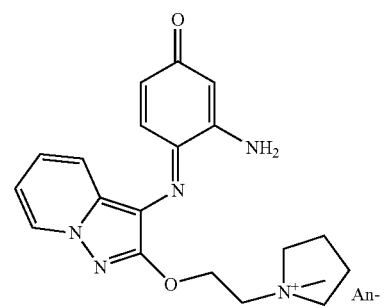
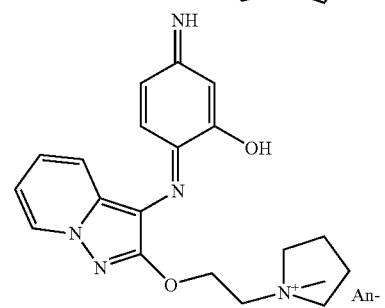
-continued
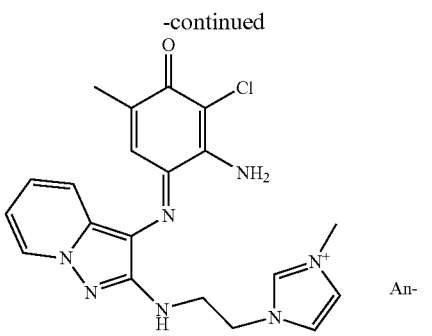
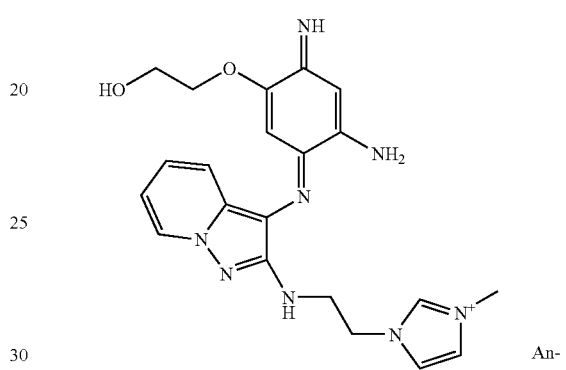
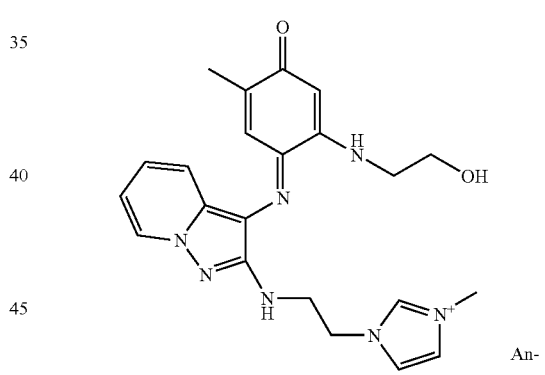
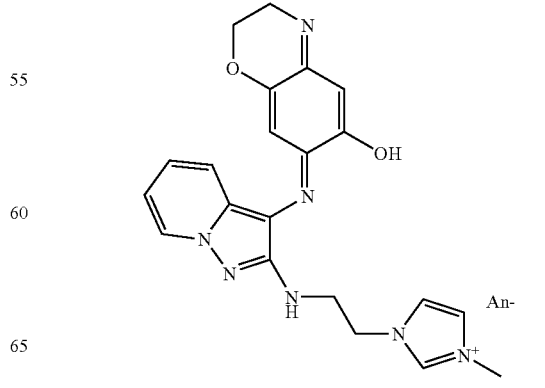

-continued
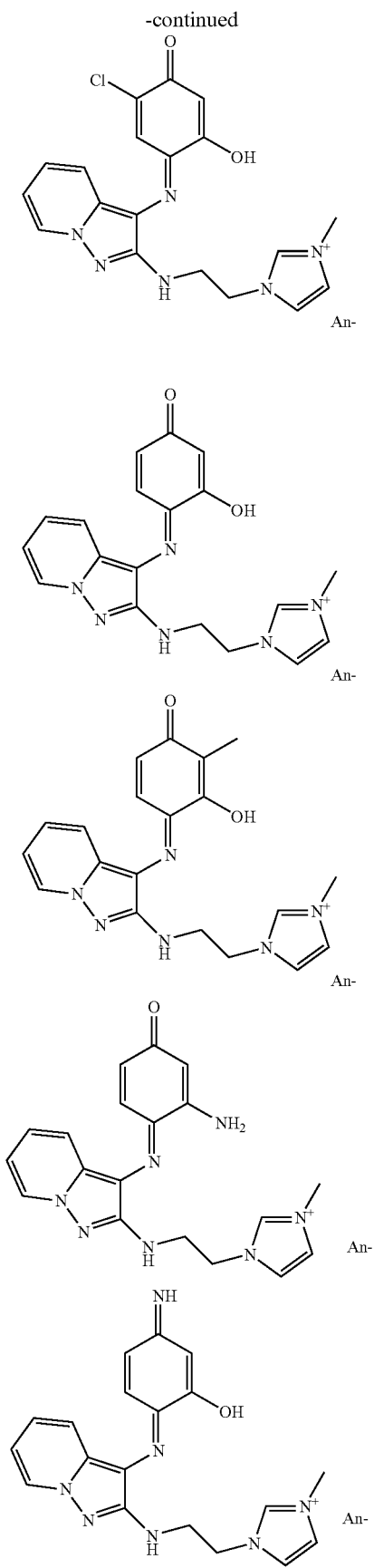
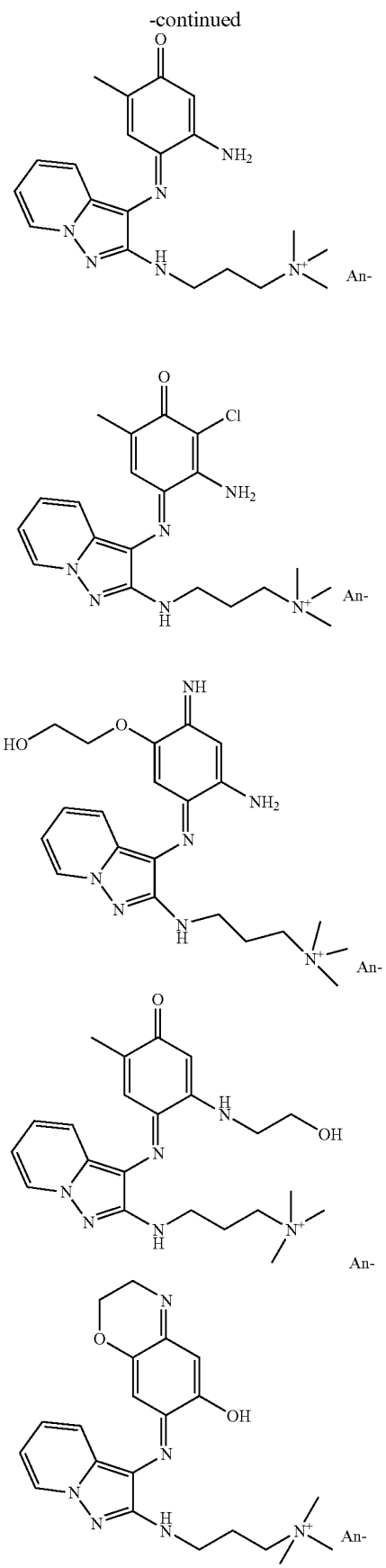

-continued
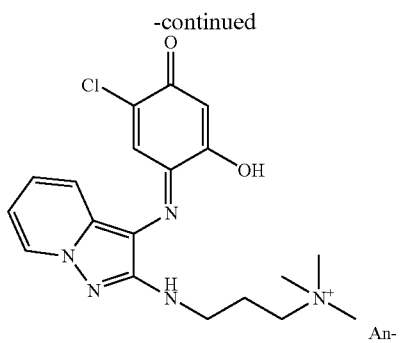
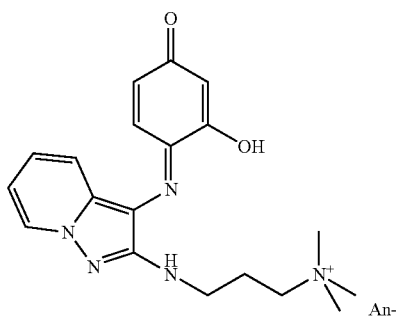
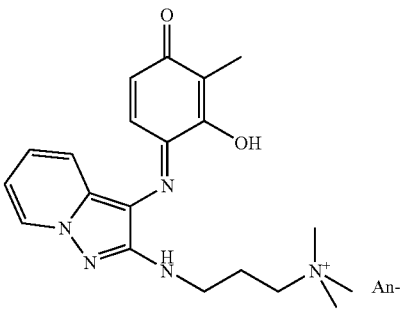
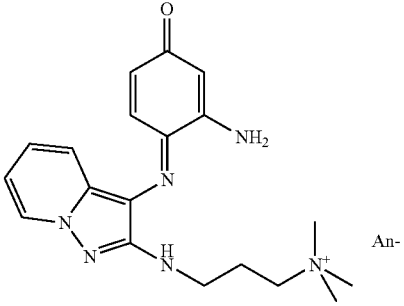
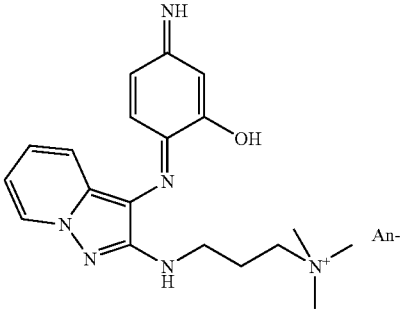
-continued
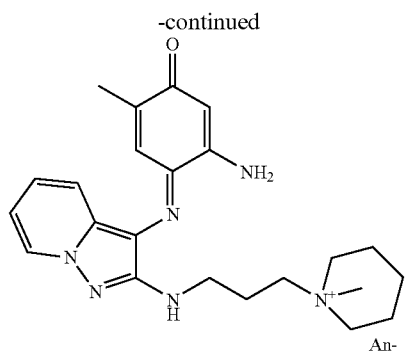
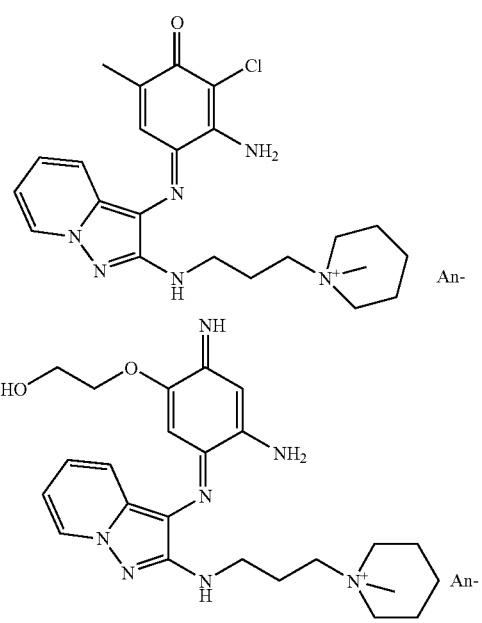
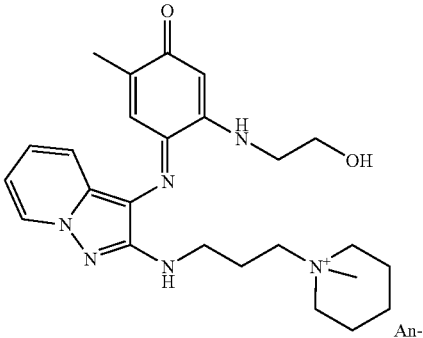
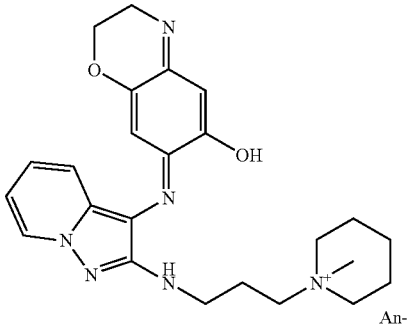

-continued
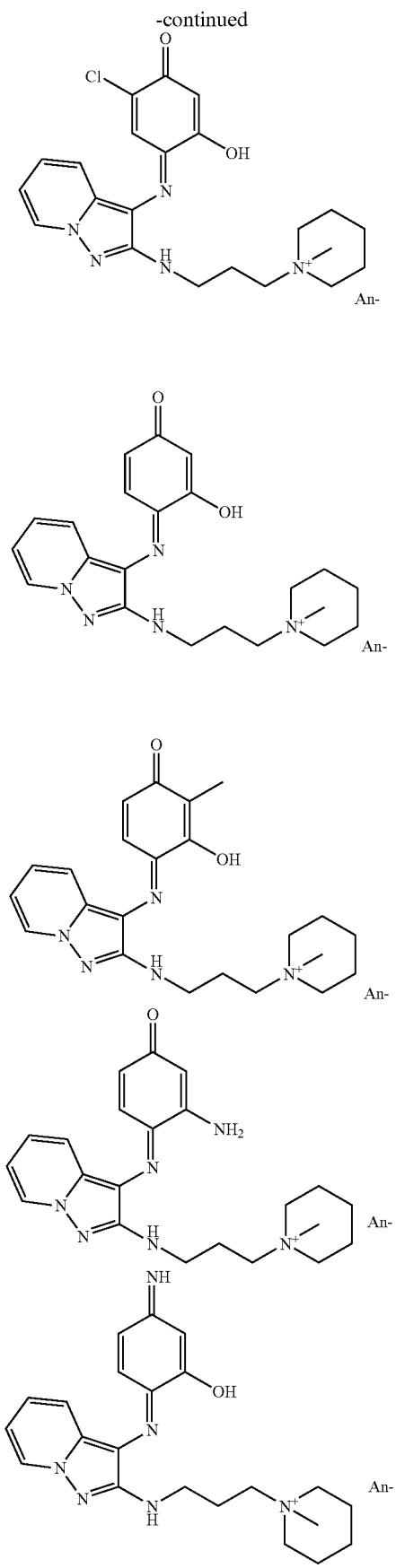
-continued
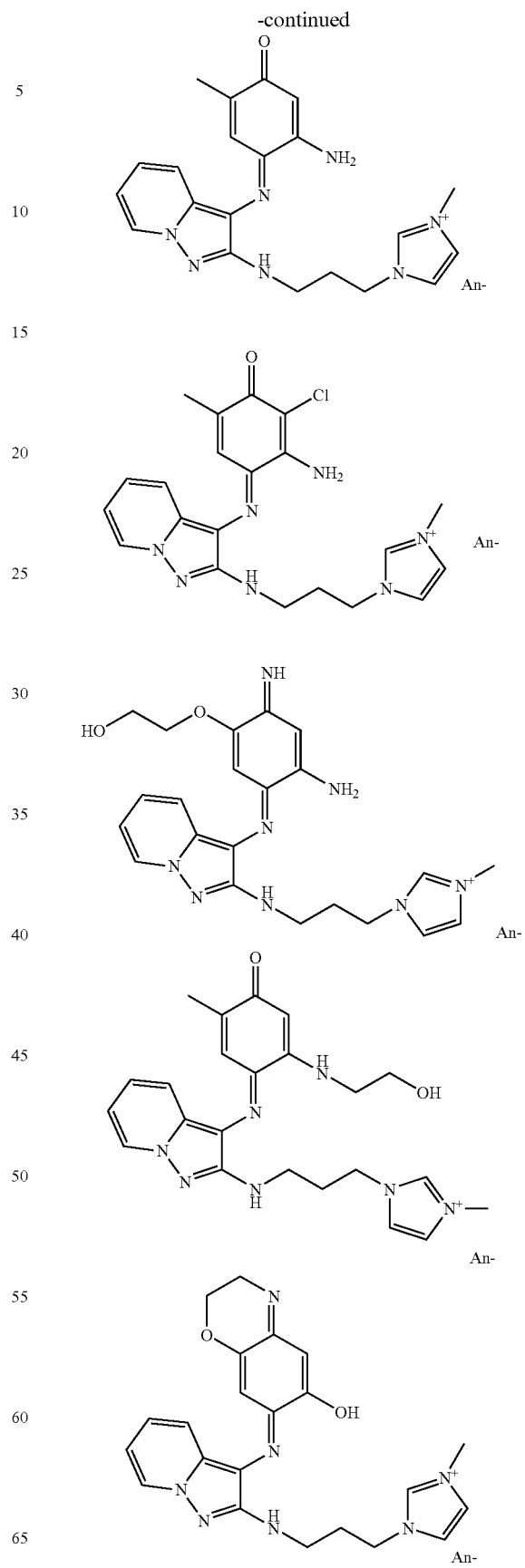

-continued
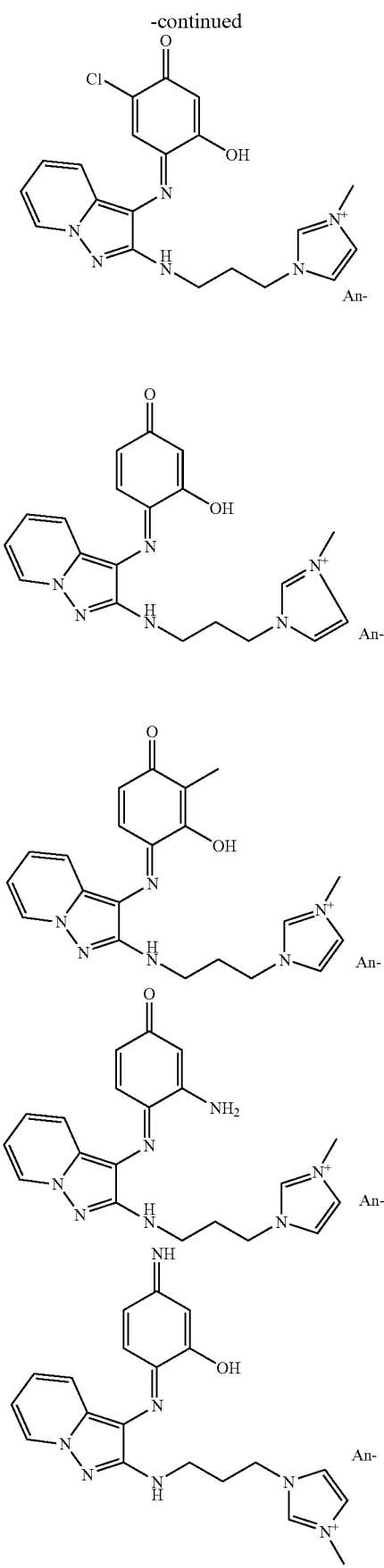
-continued
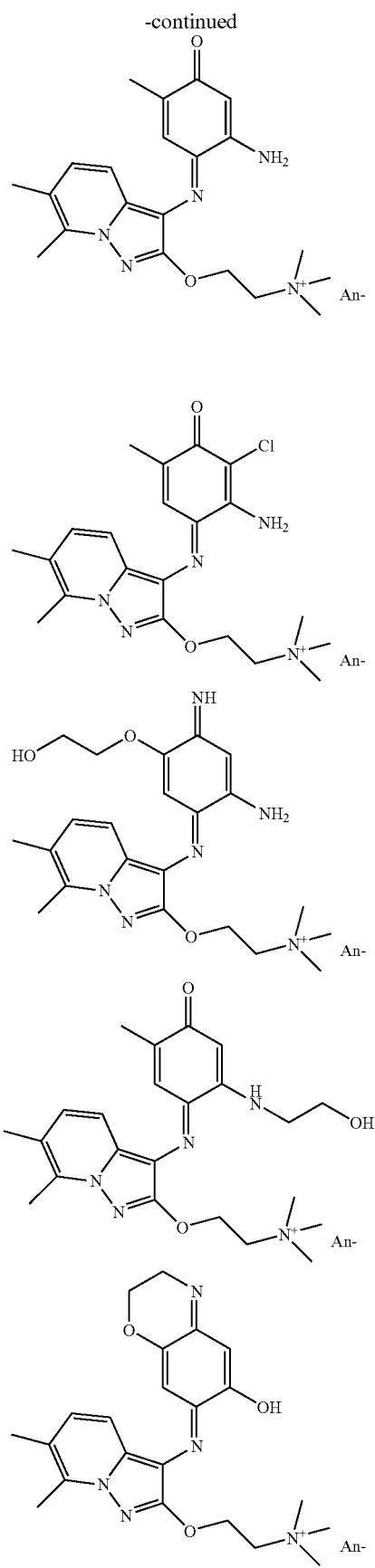

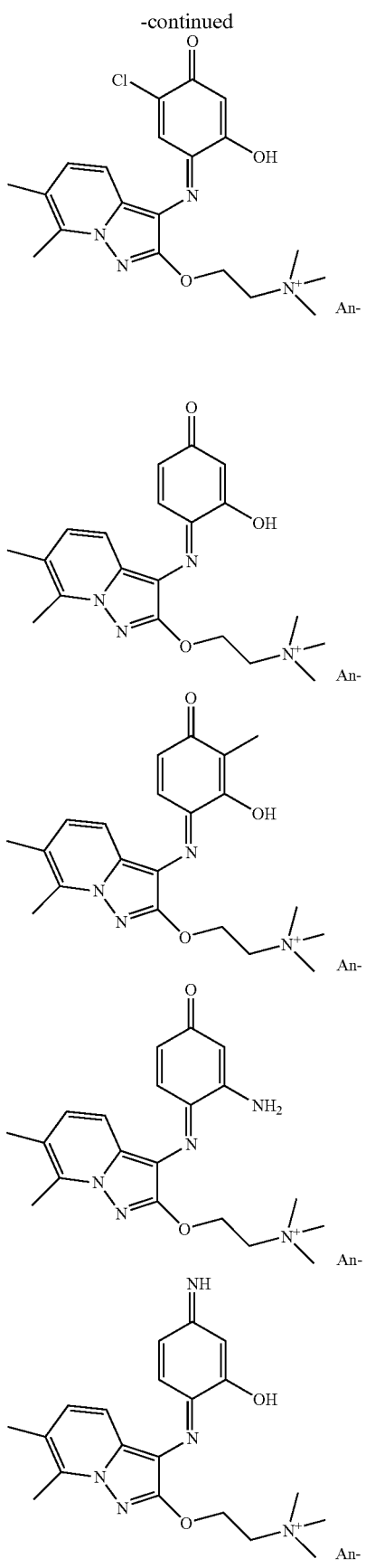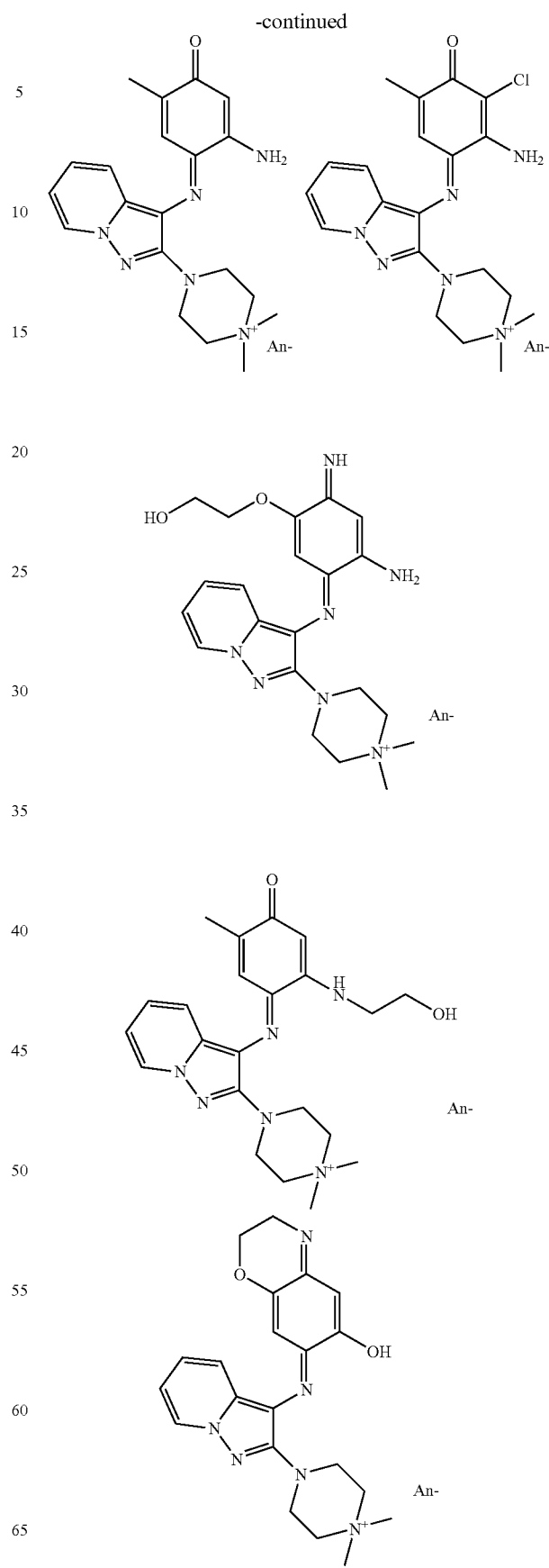

-continued

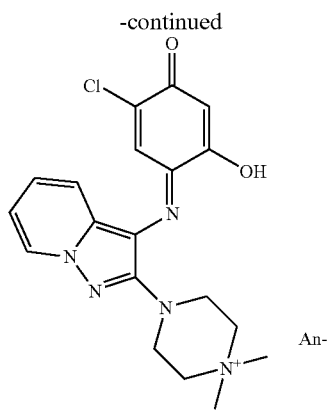
An-

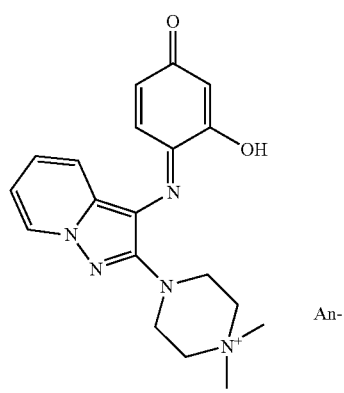
An-

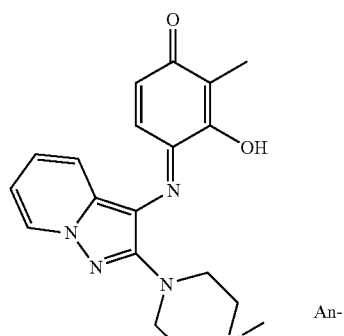
An-

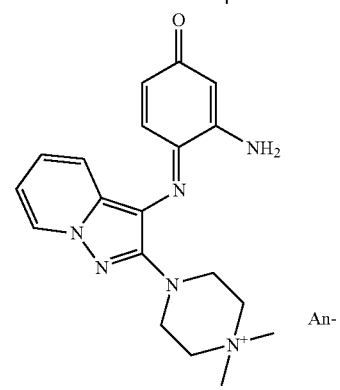
An-

-continued

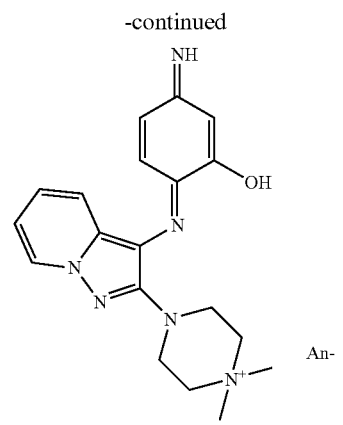
Anand also the mesomeric forms thereof, the isomeric or tautomeric forms thereof, the acid-addition salts thereof and the solvates thereof, and the corresponding leuco form compounds of formula (I).

For example, the dyes of azomethine type comprising a pyrazolopyridine unit of formula (II) can be chosen from the following compounds:

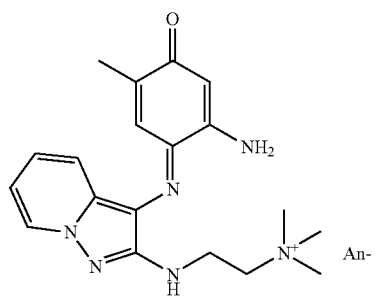
An-

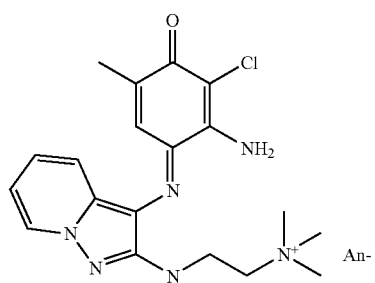
An-

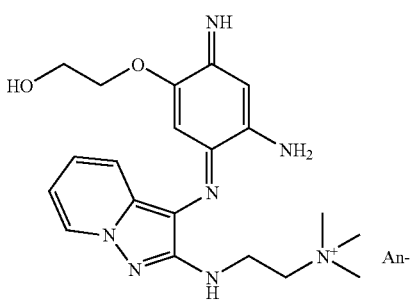
An-

-continued
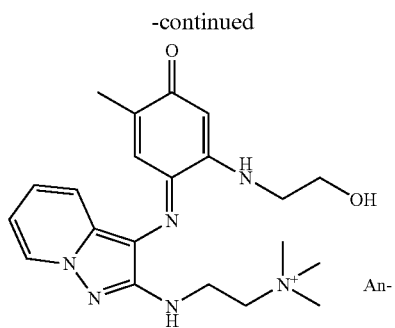
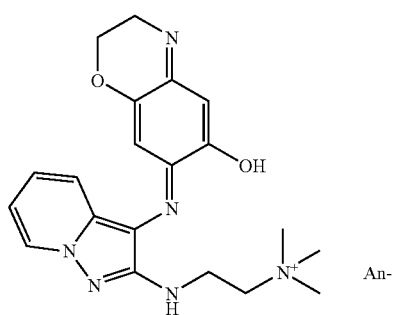
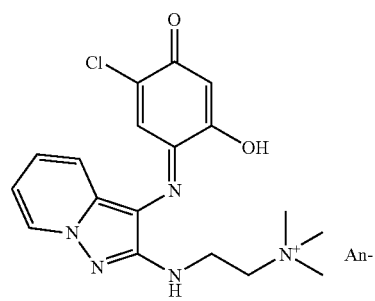
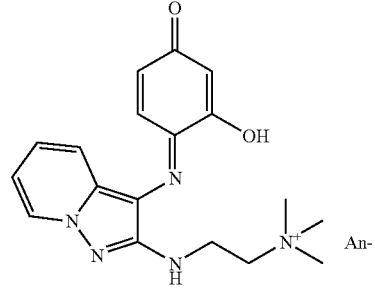
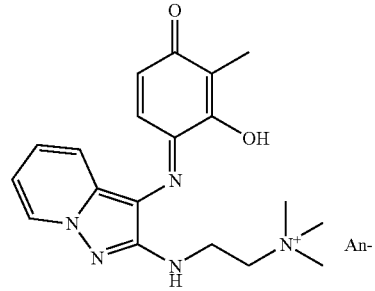
-continued
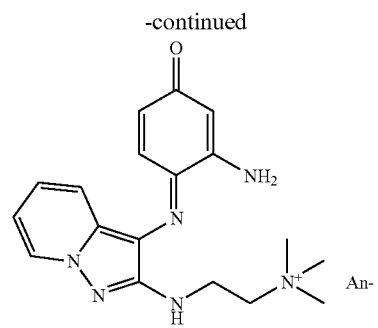
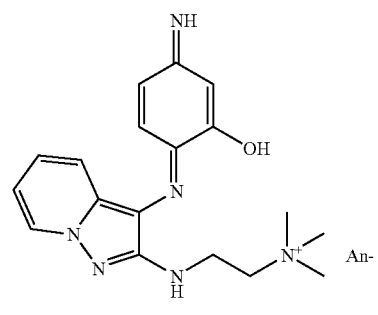
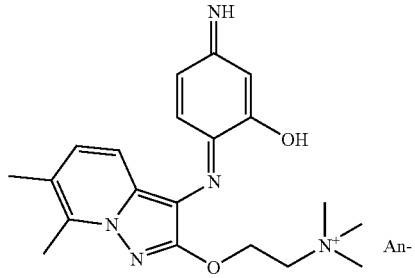
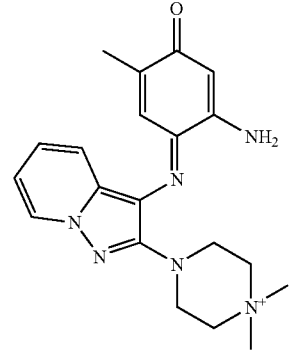
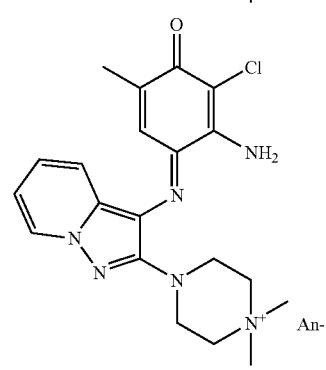

-continued
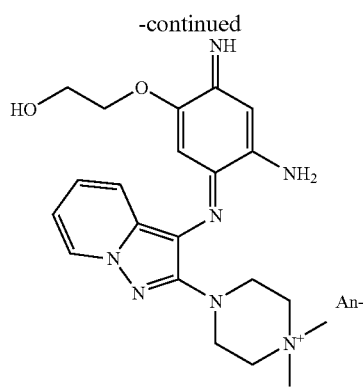
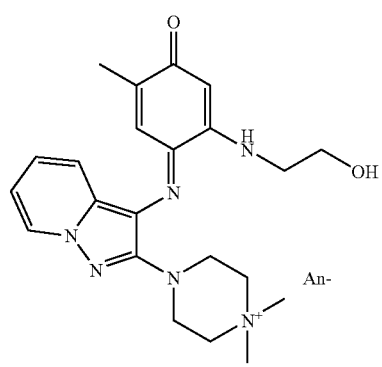
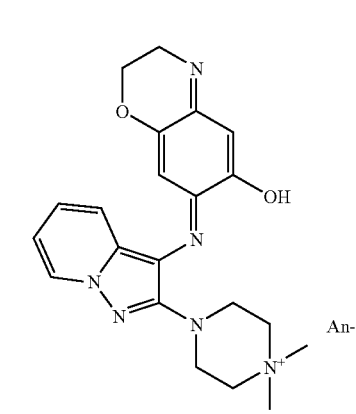
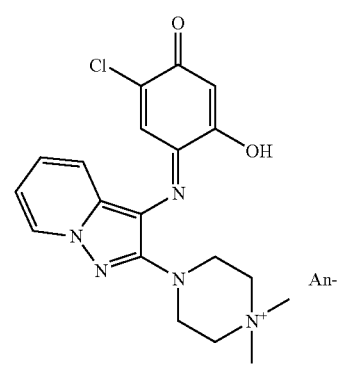
-continued
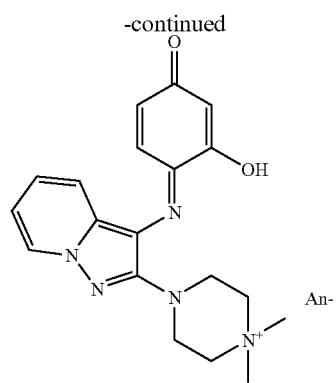
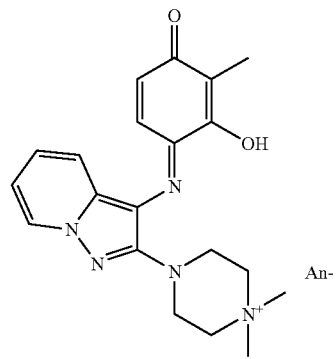
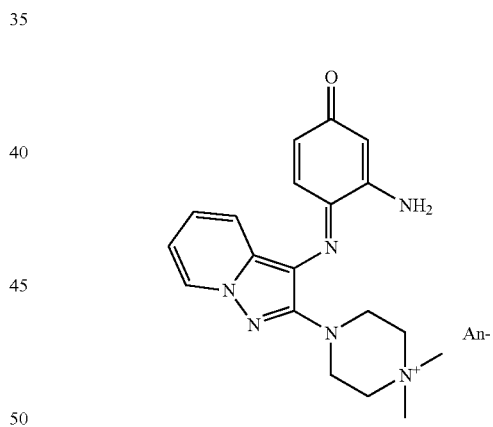
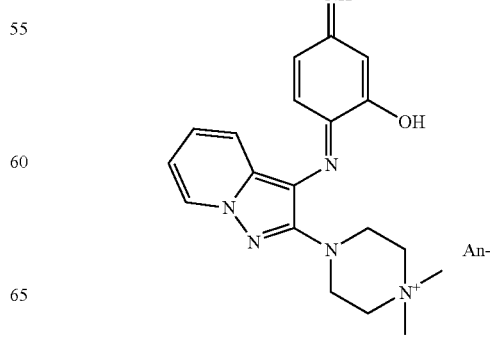

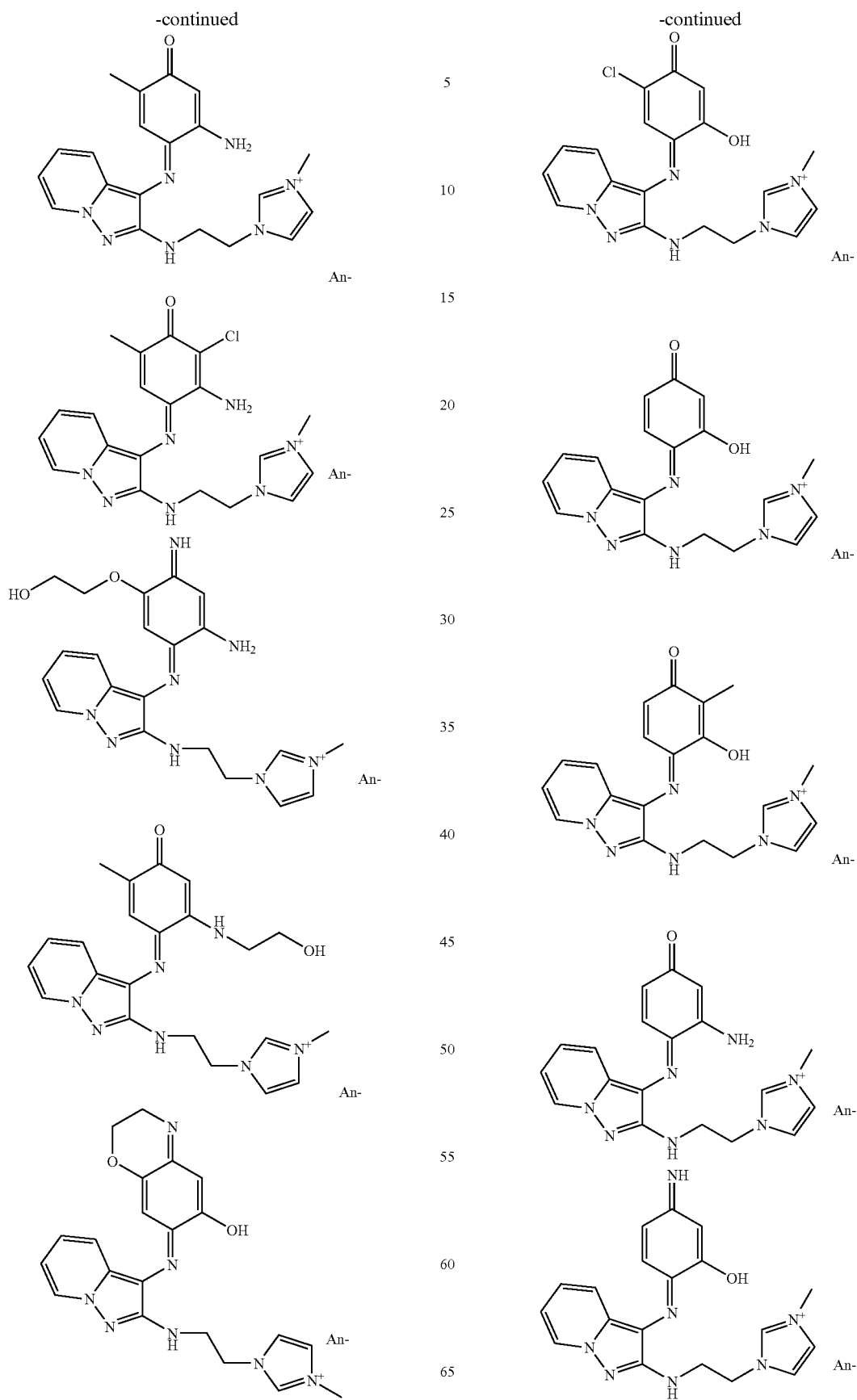

-continued
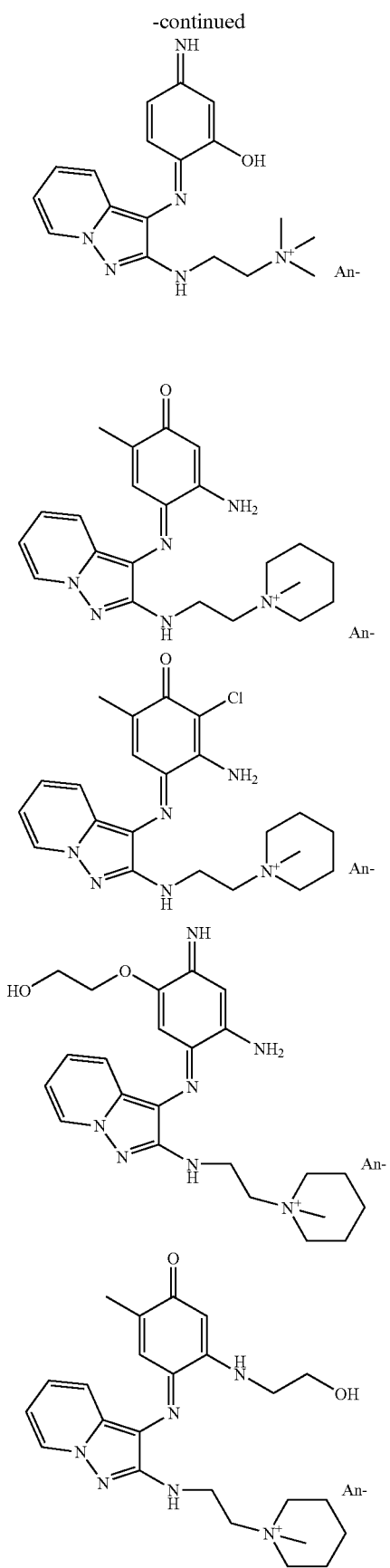
-continued
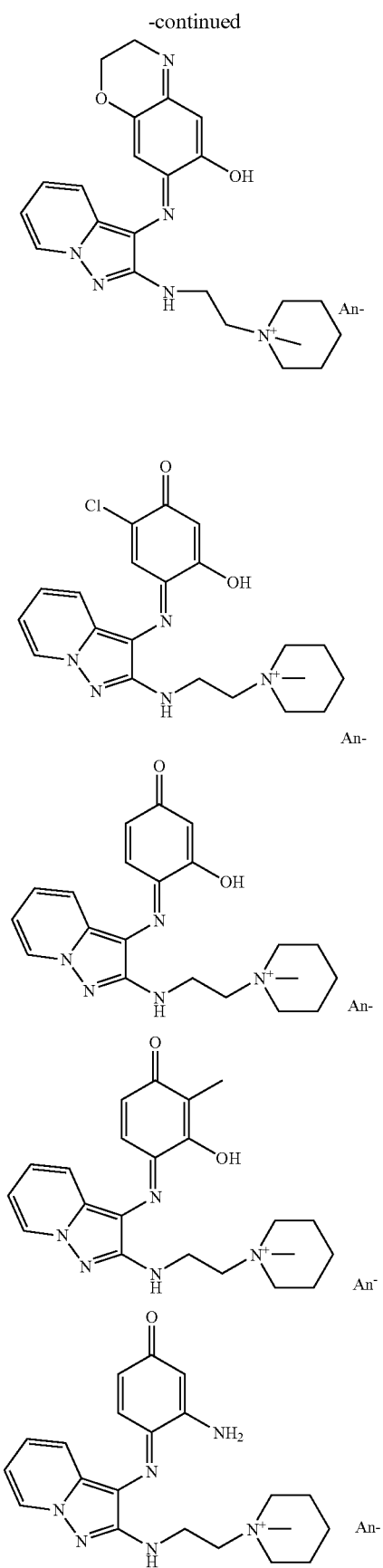

-continued
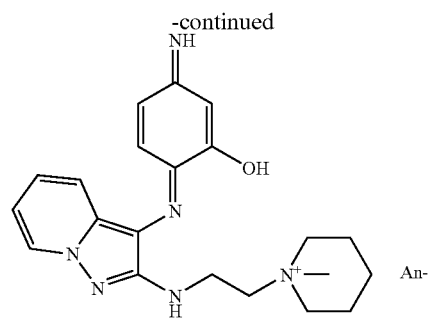
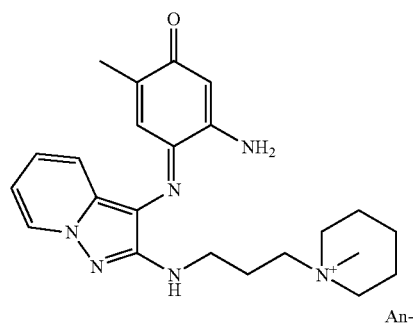
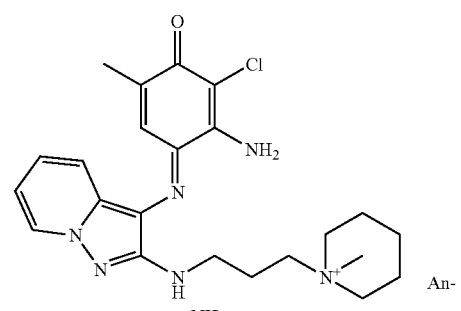
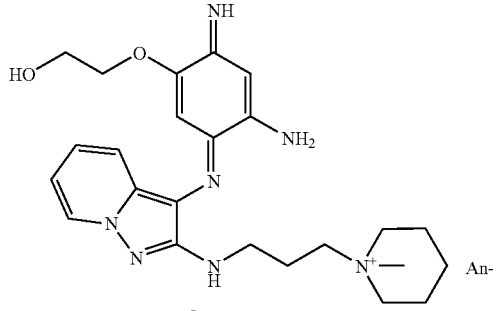
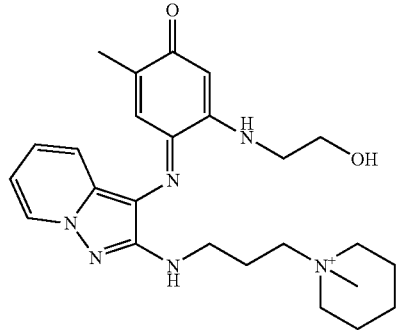
-continued
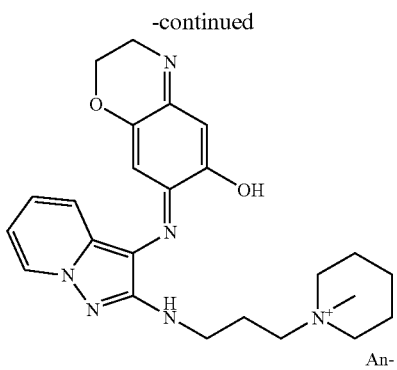
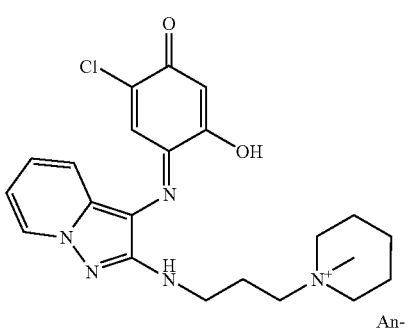
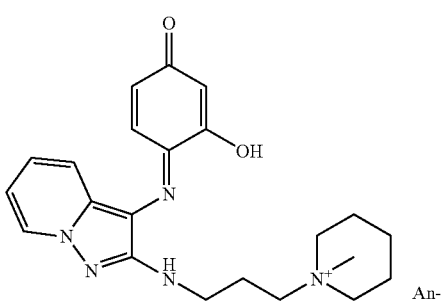
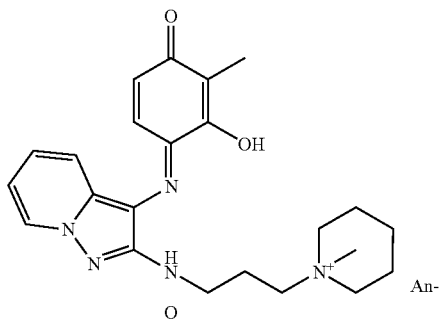
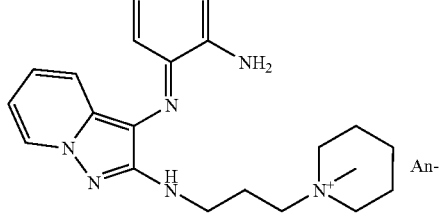

-continued
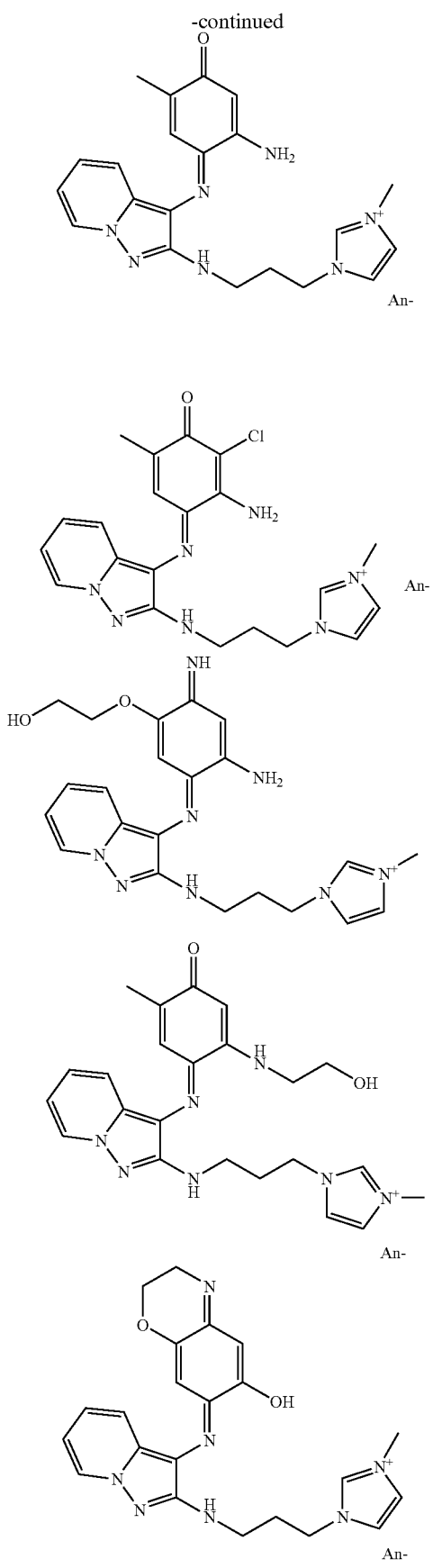
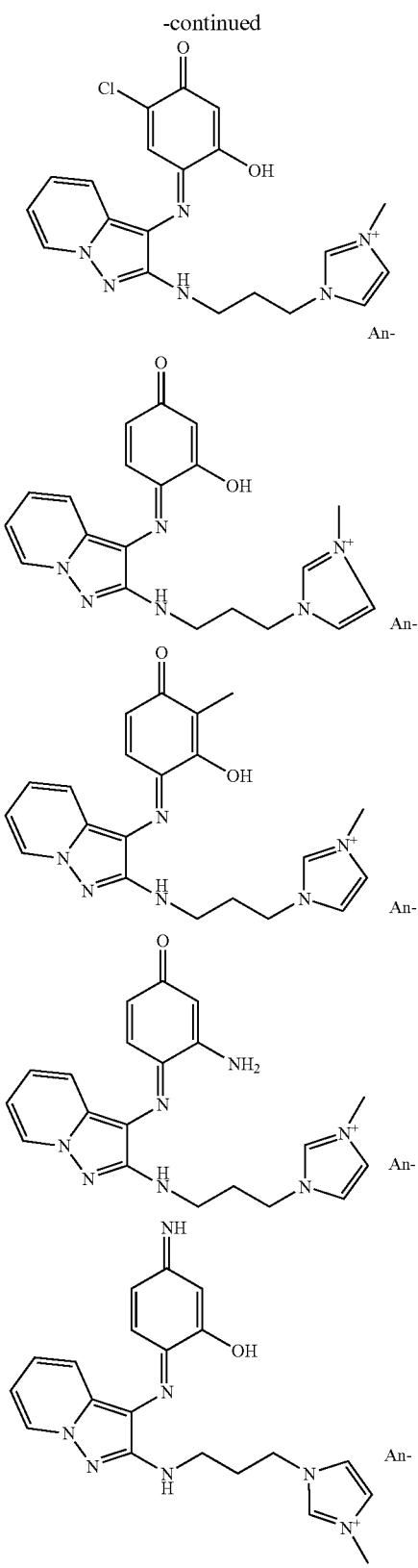
and also the isomers, mesomers, tautomers, solvates and addition salts thereof, and the corresponding leuco form compounds of formula (I).

According to at least one embodiment, the azomethine dyes are chosen from the compounds of formula (IIa) or (IIb):

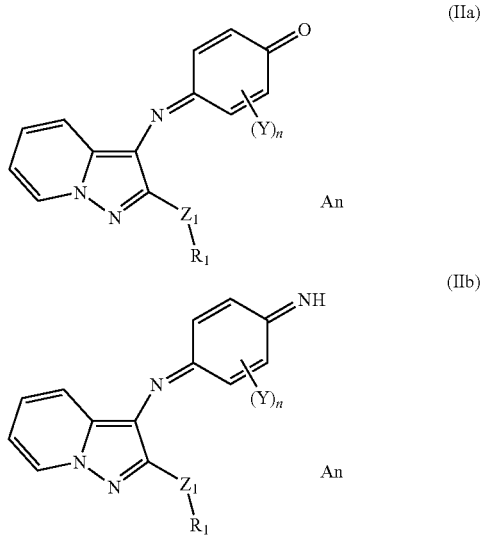

in which $R_1$ and $Z_1$, Y, n and An are as defined previously. According to at least one embodiment, $Z_1$ is chosen from an oxygen atom and a group $NR_6$. $R_1$ is for example an alkyl that may be interrupted or substituted with a quaternary ammonium radical, such as imidazolium, trialkylammonium or pyrrolidinium. When $Z_1$ is $NR_6$, then $R_1$ may form with $R_6$ a piperazinium ring.

According to another embodiment, n is 0, 1 or 2, and Y is chosen from hydroxyl, alkyl, hydroxyalkoxy, and halogen.

The compounds of formula (I) and/or (II) may be obtained according to the procedure below:

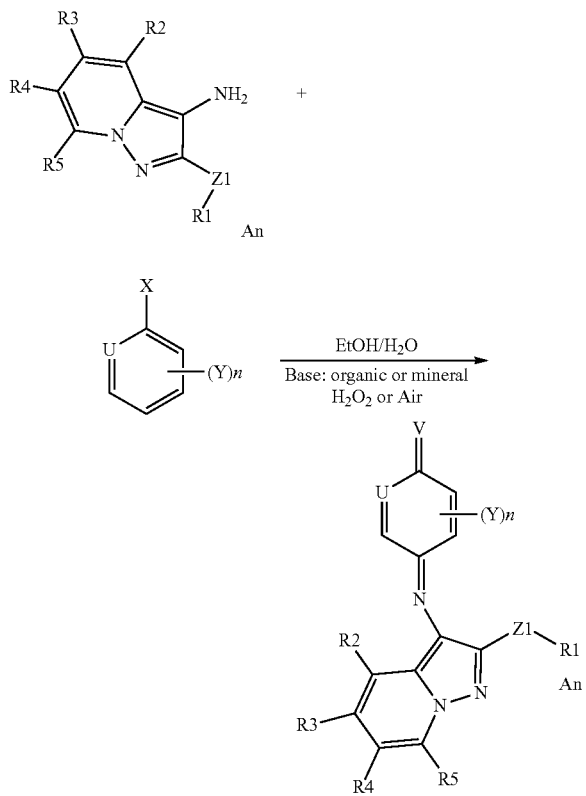

The pyrazolopyridine is weighed out in a beaker and dissolved in water and/or ethanol at room temperature. The coupler (1 equivalent) is then added, followed by aqueous ammonia or an organic or mineral base such as sodium hydroxide, potassium hydroxide, sodium carbonate, potassium carbonate, sodium acetate or potassium acetate (1 equivalent), in the presence of at least one oxidizing agent (1 equivalent or excess). The oxidizing agent(s) may be air, aqueous hydrogen peroxide solution or a chemical oxidizing agent. The reaction medium becomes colored as soon as the last two reagents are added. The reaction medium thus obtained is stirred for a period ranging from 30 minutes to 24 hours. The product formed generally precipitates from the medium. It is filtered off and then washed with water, with ethanol and with isopropyl ether. The compound recovered in powder form is dried at 20° C. under vacuum to constant weight. When there is no precipitation, the compound obtained from this reaction is recovered by evaporating off the solvent and optionally purified on a column of silica. Characterization is performed by NMR spectroscopy and/or mass spectrometry.

Provided herein is also a composition for dyeing keratin fibers, comprising, in a suitable dyeing medium, at least one compound chosen from the leuco form compounds of formula (I), the dyes of azomethine type comprising a pyrazolopyridine unit of formula (II), the mesomeric forms, isomeric forms and tautomeric forms thereof, the acid-addition salts thereof and the solvates thereof, as defined previously.

The at least one compound chosen from the leuco form compounds of formula (I), the dyes of azomethine type comprising a pyrazolopyridine unit of formula (II), the mesomeric forms, isomeric forms and tautomeric forms thereof, the acid-addition salts thereof and the solvates thereof may be present in an amount from 0.01% to 15% and such as from 0.05% to 10% by weight relative to the total weight of the composition.

The dye composition according to the disclosure may further comprise at least one oxidation base. This oxidation base(s) may be chosen from the oxidation bases conventionally used in oxidation dyeing, for example para-phenylenediamines, bis(phenyl)alkylenediamines, para-aminophenols, ortho-aminophenols and heterocyclic bases.

Examples of para-phenylenediamines that may be mentioned include para-phenylenediamine, para-tolylenediamine, 2-chloro para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2β-hydroxyethyl-para-phenylenediamine, 2-fluoro para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2β-hydroxyethyloxy-para-phenylenediamine, 2β-acetylaminoethyloxy-para-phenylenediamine, N-(β-methoxyethyl)-para-phenylenediamine, 4-aminophenylpyrrolidine, 2-thienyl-para-phenylenediamine and 2β-hydroxyethylamino-5-aminotoluene, and the acid-addition salts thereof.

Among the para-phenylenediamines mentioned above, non-limiting mention can be made of para-phenylenediamine, para-tolylenediamine, 2-isopropyl-para-phenylenediamine, 2β-hydroxyethyl-para-phenylenediamine, 2β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2β-acetylaminoethyloxy-para-phenylenediamine, and the acid-addition salts thereof.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis(4-aminophenyl)tetra-methylenediamine, N,N'-bis(4-methyl-aminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the acid-addition salts thereof.

Among the para-aminophenols, examples that may be mentioned include para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol and 4-amino-2-fluorophenol, and the acid-addition salts thereof.

Among the ortho-aminophenols, examples that may be mentioned include 2-aminophenol, 2-amino-5-methylphenol, 2-amino-6-methylphenol and 5-acetamido-2-aminophenol, and the acid-addition salts thereof.

Among the heterocyclic bases, examples that may be mentioned include pyridine derivatives, pyrimidine derivatives and pyrazole derivatives, and derivatives of pyrazolo[1,2a]pyrazol-1-one type.

Among the pyridine derivatives, non-limiting mention may be made of the compounds described, for example, in patents GB 1 026 978 and GB 1 153 196, for instance 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid-addition salts thereof.

Among the pyrimidine derivatives, non-limiting mention may be made, for example, of the compounds described in patents DE 2 359 399; JP 88-169 571; JP 05 163 124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048, and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl) amino]ethanol, 2-[(7-amino-pyrazolo[1,5-a]pyrimidin-3-yl)(-2-hydroxyethyl)amino]-ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]-pyrimidine-3,7-diamine and 3-amino-5-methyl-7-imidazolylpropylaminopyrazolo[1,5-a]pyrimidine, and the acid-addition salts thereof and the tautomeric forms thereof, when a tautomeric equilibrium exists.

Among the pyrazole derivatives, non-limiting mention may be made of the compounds described in patents DE 3 843 892 and DE 4 133 957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl 3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino 3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino 1-methylpyrazole, and the acid-addition salts thereof.

Among the derivatives of pyrazolo[1,2a]pyrazol-1-one type, non-limiting mention may be made of 2,3-diamino-6, 7-dihydro-1H, and 5H-pyrazolo[1,2a]pyrazol-1-one.

The dye composition according to the disclosure may comprise at least one coupler conventionally used for the dyeing of keratin fibers. Among these couplers, non-limiting mention may be made of meta-phenylenediamines, meta-aminophenols, meta-diphenols, naphthalene-based couplers and heterocyclic couplers.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1β-hydroxyethylamino-3, 4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine 3,5-diamino-2,6-dimethoxypyridine, 1N-(β-hydroxyethyl)amino-3,4-methylenedioxybenzene end 2,6-bis(β-hydroxyethylamino)toluene, and the acid-addition salts thereof.

In the dye composition according to the disclosure, the at least one oxidation base can be present in an amount ranging from 0.001% to 10% and such as from 0.005% to 6% by weight relative to the total weight of the composition. The at least one coupler can be present in an amount ranging from 0.001% to 10% and such as from 0.005% to 6% by weight relative to the total weight of the composition.

For example, the acid used in the acid-addition salts for the oxidation bases and couplers can be chosen from the hydrochlorides, hydrobromides, sulfates, citrates, succinates, tartrates, lactates, tosylates, benzenesulfonates, phosphates and acetates.

The dye composition may optionally further comprise at least one additional direct dye conventionally used for the dyeing of keratin fibers. This additional direct dye may be chosen from cationic and nonionic species.

Non-limiting examples that may be mentioned include nitrobenzene dyes, azo, azomethine, methine, tetraazapentamethine, anthraquinone, naphthoquinone, benzoquinone, phenothiazine, indigoid, xanthine, phenanthridine and phthalocyanin dyes, triarylmethane-based dyes and natural dyes, alone or as mixtures.

The at least one additional direct dye may be chosen, for example, from the following red or orange nitrobenzene dyes: 1-hydroxy-3-nitro-4-N-(γ-hydroxypropyl)aminobenzene, N-(β-hydroxyethyl)amino-3-nitro-4-aminobenzene, 1-amino-3-methyl-4-N-(β-hydroxyethyl)amino-6-nitrobenzene, 1-hydroxy-3-nitro-4-N-(β-hydroxyethyl)aminobenzene, 1,4-diamino-2-nitrobenzene, 1-amino-2-nitro-4-methylaminobenzene, N-(β-hydroxyethyl)-2-nitro-paraphenylenediamine, 1-amino-2-nitro-4-(β-hydroxyethyl) amino-5-chlorobenzene, 2-nitro-4-aminodiphenylamine, 1-amino-3-nitro-6-hydroxybenzene, 1-(β-aminoethyl) amino-2-nitro-4-(β-hydroxyethyloxy)benzene, 1-(β,γ-dihydroxypropyl)oxy-3-nitro-4-(β-hydroxyethyl)aminobenzene, 1-hydroxy-3-nitro-4-aminobenzene, 1-hydroxy-2-amino-4,6-dinitrobenzene, 1-methoxy-3-nitro-4-(β-hydroxyethyl)-aminobenzene, 2-nitro-4'-hydroxydiphenylamine, 1-amino-2-nitro-4-hydroxy-5-methylbenzene.

The at least one additional direct dye may also be chosen from yellow and green-yellow nitrobenzene direct dyes. Examples that may be mentioned include the compounds chosen from: 1β-hydroxyethyloxy-3-methylamino-4-nitrobenzene, 1-methylamino-2-nitro-5-(β,γ-dihydroxypropyl)oxybenzene, 1-(β-hydroxyethyl)amino-2-methoxy-4-nitrobenzene, 1-(β-aminoethyl)amino-2-nitro-5-methoxybenzene, 1,3-bis(β-hydroxyethyl)amino-4-nitro-6-chlorobenzene, 1-amino-2-nitro-6-methylbenzene, 1-(β-hydroxyethyl)amino-2-hydroxy-4-nitrobenzene, N-(β-hydroxyethyl)-2-nitro-4-trifluoromethylaniline, 4-(β-hydroxyethyl)amino-3-nitrobenzenesulfonic acid, 4-ethylamino-3-nitrobenzoic acid, 4-(β-hydroxyethyl) amino-3-nitrochlorobenzene, 4-(β-hydroxyethyl)amino-3-nitromethylbenzene, 4-(β,γ-dihydroxypropyl)amino-3-nitrotrifluoro-methylbenzene, 1-(β-ureidoethyl)amino-4-nitrobenzene, 1,3-diamino-4-nitrobenzene, 1-hydroxy-2-amino-5-nitrobenzene, 1-amino-2-[tris(hydroxymethyl) methyl]amino-5-nitrobenzene, 1-(β-hydroxyethyl)amino-2-nitrobenzene and 4-(β-hydroxyethyl)amino-3-nitrobenzamide.

Non-limiting mention may also be made of blue or violet nitrobenzene direct dyes, for instance 1-(β-hydroxyethyl) amino-4-N,N-bis(β-hydroxyethyl)amino-2-nitrobenzene, 1-(γ-hydroxypropyl)amino-4-N,N-bis(β-hydroxyethyl) amino-2-nitrobenzene, 1-(β-hydroxyethyl)amino-4-(N-methyl-N-β-hydroxyethyl)amino-2-nitrobenzene, 1-(β-hydroxyethyl)amino-4-(N-ethyl-N-β-hydroxyethyl)amino-2-nitrobenzene, 1-(β,γ-dihydroxy-propyl)amino-4-(N-ethyl-N-β-hydroxyethyl)amino-2-nitrobenzene, the 2-nitro-paraphenylenediamines of formula (III) below:

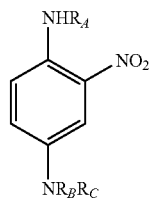

(III)

in which:
$R_B$ represents a $C_1$-$C_4$ alkyl, a β-hydroxyethyl, β-hydroxypropyl or γ-hydroxypropyl;

$R_A$ and $R_C$, which may be identical or different, represent a β-hydroxyethyl, β-hydroxypropyl, γ-hydroxypropyl or β,γ-dihydroxypropyl, and at least one of the radicals $R_B$, $R_C$ and $R_A$ represents a γ-hydroxypropyl, and $R_A$ and $R_C$ do not simultaneously represent a β-hydroxyethyl radical when $R_B$ is a γ-hydroxypropyl radical, such as those described in French patent application FR 2 692 572.

Among the azo direct dyes according to the disclosure, non-limiting mention may be made of the cationic azo dyes described in patent applications WO 95/15144, WO 95/01772, EP 714954, FR 2 822 696, FR 2 825 702, FR 2 825 625, FR 2 822 698, FR 2 822 693, FR 2 822 694, FR 2 829 926, FR 2 807 650, WO 02/078660, WO 02/100834, WO 02/100369 and FR 2 844 269.

Among these compounds, non-limiting mention may be made of the following dyes: 1,3-dimethyl-2-[[4-(dimethylamino)phenyl]azo]-1H-imidazolium chloride, 1,3-dimethyl-2-[(4-aminophenyl)azo]-1H-imidazolium chloride, 1-methyl-4-[(methylphenylhydrazono)methyl]-pyridinium methyl sulfate.

Among the azo direct dyes, further non-limiting mention may be made of the following dyes, described in the COLOR INDEX INTERNATIONAL 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Non-limiting mention may also be made of 1-(4'-aminodiphenylazo)-2-methyl-4,4-bis(β-hydroxyethyl)aminobenzene and 4-hydroxy-3-(2-methoxyphenylazo)-1-naphthalenesulfonic acid.

Among the quinone direct dyes, non-limiting mention may be made the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds: 1-N-methylmorpholiniumpropylamino-4-hydroxyanthraquinone, 1-aminopropylamino-4-methylaminoanthraquinone, 1-aminopropylamino-anthraquinone, 5β-hydroxyethyl-1,4-diaminoanthraquinone, 2-aminoethylaminoanthraquinone, and 1,4-bis(β,γ-dihydroxypropylamino)anthraquinone.

Among the azine dyes, non-limiting mention may be made of the following compounds: Basic Blue 17, Basic Red 2.

Among the triarylmethane dyes according to the disclosure, non-limiting mention may be made of the following compounds: Basic Green 1, Acid Blue 9, Basic Violet 3, Basic Violet 14, Basic Blue 7, Acid Violet 49, Basic Blue 26, and Acid Blue 7.

Among the indoamine dyes according to the disclosure, non-limiting mention may be made of the following compounds: 2β-hydroxyethlyamino-5-[bis(β-4'-hydroxyethyl) amino]anilino-1,4-benzoquinone, 2β-hydroxyethylamino-5-(2'-methoxy-4'-amino)anilino-1,4-benzoquinone, 3-N-(2'-chloro-4'-hydroxy)phenylacetylamino-6-methoxy-1,4-benzoquinoneimine, 3-N-(3'-chloro-4'-methylamino) phenylureido-6-methyl-1,4-benzoquinone imine, 3-[4'-N-(ethyl, and carbamylmethyl)amino]phenyl-ureido-6-methyl-1,4-benzoquinoneimine.

Among the dyes of tetraazapentamethine type according to the disclosure, non-limiting mention may be made of the following dyes: 2-((E)-{(E)-[(1,3-dimethyl-1,3-dihydro-2H-imidazol-2-ylidene)hydrazono]methyl}diazenyl)-1,3-dimethyl-1H-imidazol-3-ium chloride; 2-{(E)-[(1Z)-N-(1,3- dimethyl-1,3-dihydro-2H-imidazol-2-ylidene)ethanehydrazonoyl]diazenyl}-1,3-dimethyl-1H-imidazol-3-ium chloride; 4-methoxy-2-((E)-{(1E)-1-[(2E)-(4-methoxy-1-methylpyrid-2(1H)-ylidene)hydrazono]ethyl}diazenyl)-1-methylpyridinium chloride; 1-methyl-2-((E)-{(1E)-1-[(2E)-(1-methylpyrid-2(1H)-ylidene)hydrazono]ethyl}diazenyl) pyridinium chloride; 1-(2-hydroxyethyl)-2-[(E)-((1E)-1-{(2E)-[1-(2-hydroxyethyl)pyrid-2(1H)-ylidene] hydrazono}ethyl)diazenyl]pyridinium chloride; 1-methyl-2-((E)-{(E)-[(2Z)-(1-methylpyrid-2(1H)-ylidene)hydrazono] methyl}diazenyl)-pyridinium chloride; and 1-(2-hydroxyethyl)-2-[(E)-((E)-{(2E)-[1-(2-hydroxyethyl)pyrid-2(1H)-ylidene]hydrazono}methyl)diazenyl]pyridinium acetate.

Among the natural additional direct dyes according to the disclosure, non-limiting mention may be made of lawsone, juglone, alizarin, purpurin, carminic acid, kermesic acid, purpurogallin, protocatechaldehyde, indigo, isatin, curcumin, spinulosin and apigenidin. It is also possible to use extracts or decoctions comprising these natural dyes, such as henna-based poultices or extracts.

The at least one additional direct dye may present in the composition in an amount ranging from 0.001% to 20% and such as from 0.01% to 10% by weight relative to the weight of the composition.

The medium that is suitable for dyeing, also known as the dye support, may comprise water or a mixture of water and of at least one organic solvent to dissolve the compounds that are not sufficiently water-soluble.

For example, the at least one organic solvent is chosen from linear and branched, such as saturated, monoalcohols and diols, comprising from 2 to 10 carbon atoms, such as ethyl alcohol, isopropyl alcohol, hexylene glycol (2-ethyl-2,4-pentanediol), neopentyl glycol and 3-ethyl-1,5-pentanediol; aromatic alcohols such as benzyl alcohol and phenylethyl alcohol; glycols or glycol ethers, for instance ethylene glycol monomethyl, monoethyl or monobutyl ether, propylene glycol or ethers thereof, for instance propylene glycol monomethyl ether, butylene glycol and dipropylene glycol; and also diethylene glycol alkyl ethers, such as $C_1$-$C_4$, for instance diethylene glycol monoethyl ether and monobutyl ether.

The at least one organic solvent described above may be present in an amount ranging from 1% to 40% by weight and such as from 5% to 30% by weight relative to the total weight of the composition.

The dye composition may also comprise at least one adjuvant conventionally used in dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and for example anionic, cationic, nonionic or amphoteric associative polymers, antioxidants, penetrants, sequestrants, fragrances, buffers, dispersants, conditioning agents, for instance volatile or non-volatile, modified or unmodified silicones, film-forming agents, ceramides, preserving agents, stabilizers and opacifiers.

The at least one adjuvant can be generally present in an amount ranging from 0.01% to 20% by weight relative to the weight of the composition.

Needless to say, a person skilled in the art will take care to select this or these optional additional compound(s) such that the beneficial properties intrinsically associated with the dye composition according to the disclosure are not, or are not substantially, adversely affected by the envisaged addition(s).

The pH of the dye composition according to the disclosure can range from 3 to 12 and for example from 5 to 11. It may be adjusted to the desired value via acidifying or basifying agents usually used in the dyeing of keratin fibers, or alternatively using standard buffer systems. Modification of the pH within these ranges can promote the formation of compounds (I) or (II).

Among the acidifying agents, examples that may be mentioned include mineral acids, for instance hydrochloric acid, nitric acid or sulfuric acid, or organic acids, for instance compounds comprising at least one carboxylic acid function, for instance acetic acid, tartaric acid, citric acid or lactic acid, a sulfonic acid function, a phosphonic acid function or a phosphoric acid function.

Among the basifying agents, examples that may be mentioned include aqueous ammonia, alkali metal carbonates, alkanolamines such as monoethanolamine, diethanolamine and triethanolamine, and also derivatives thereof, sodium hydroxide, potassium hydroxide and the compounds of formula (IV) below:

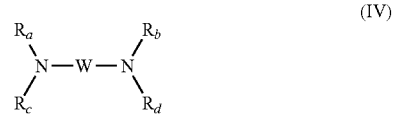

(IV)

in which W is a propylene residue optionally substituted with a hydroxyl group or a $C_1$-$C_4$ alkyl; Ra, Rb, Rc and Rd, which may be identical or different, represent a hydrogen atom, a $C_1$-$C_4$ alkyl or a $C_1$-$C_4$ hydroxyalkyl.

The compounds of formula (II) may be obtained from the compounds of formula (I) by reaction with atmospheric oxygen or via the action of at least one oxidizing agent, which may be any oxidizing agent conventionally used in the field, and can be chosen from hydrogen peroxide, urea peroxide, alkali metal bromates, persalts such as perborates and persulfates, and also enzymes, among which mention may be made of peroxidases, 2-electron oxidoreductases such as uricases, and 4-electron oxygenases, for instance laccases.

The at least one oxidizing agent can also contribute to obtaining simultaneous lightening of keratin fibers (lightening dyeing) when the composition comprises oxidation bases or couplers.

The dye composition may be in various forms, such as in the form of liquids, creams or gels, or in any other form that is suitable for dyeing keratin fibers, such as human hair.

The coloration obtained may depend on the compounds applied to the keratin fibers. The coloration is more intense when all these compounds are in the form of dyes of azomethine type comprising a pyrazolopyridine unit, i.e. when they are of formula (II). By promoting the formation of compounds of formula (I) from the compounds of formula (II), the intensity of the coloration may be reduced until it has disappeared.

Provided herein is a method for dyeing keratin fibers comprising applying to the keratin fibers at least one composition comprising at least one compound chosen from of the leuco form compounds of formula (I), the dyes of azomethine type comprising a pyrazolopyridine unit of formula (II) as defined previously, and also the mesomeric forms, isomeric forms and tautomeric forms thereof, the acid-addition salts thereof and the solvates thereof, as defined previously.

According to at least one embodiment, the at least one composition comprises compounds of formula (II).

When the oxidizing agent is used, it may be present in the at least one composition of the disclosure. It may also be applied separately, as a pretreatment or a post-treatment.

The application of the at least one composition of the present disclosure may or may not be followed by rinsing.

The leave-on time of the at least one composition can range from 3 to 60 minutes, such as from 5 to 40 minutes and further such as from 10 to 30 minutes.

The application temperature can be at room temperature, or at a temperature ranging from 25 to 55° C.

Provided herein is also a multi-compartment device or kit for performing the keratin fiber dyeing process described above.

The multi-compartment device of the disclosure comprises at least one first compartment comprising at least one composition comprising at least one compound of formula (I), and at least one second compartment comprising at least one oxidizing agent, and optionally at least one compound of formula (II), and at least one alkaline agent.

This device may be equipped with an applicator for applying the desired mixture to the hair, such as the devices described in patent FR 2 586 913.

The examples that follow serve to illustrate the disclosure without, however, being limiting in scope.

EXAMPLES

Examples of Synthesis

Example 1

Synthesis of 2-[(3-{[(1E)-2-amino-5-methyl-4-oxo-cyclohexa-2,5-dien-1-ylidene]amino}pyrazolo[1,5-a]pyridin-2-yl)amino]-N,N,N-trimethylethanaminium chloride

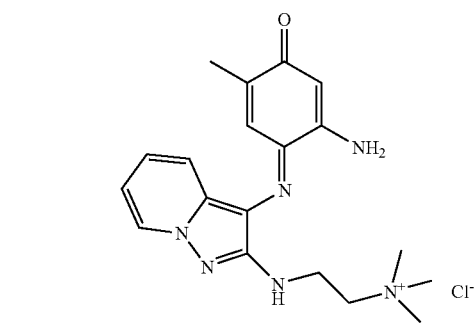

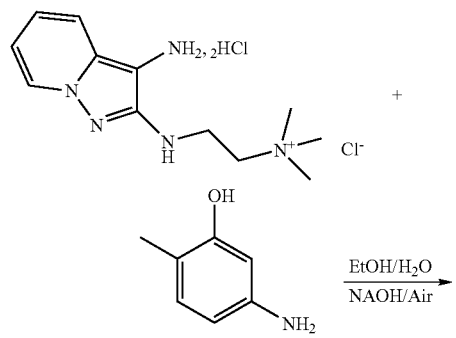

-continued

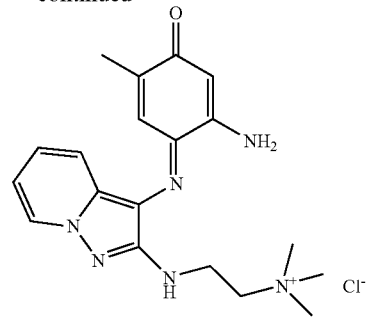

5.83 mmol of 2-[(3-aminopyrazolo[1,5-a]pyridin-2-yl)amino]-N,N,N-trimethylethanaminium chloride hydrochloride dissolved in 20 ml of ethanol and 10 ml of water were placed in a 100 ml one-necked round-bottomed flask.

5.83 mmol of 5-amino-2-methylphenol and then 29.18 mmol of sodium hydrogen carbonate were added to this solution.

The reaction medium became colored as soon as the last two reagents were added. The reaction took place at room temperature.

After leaving overnight, the solvent was evaporated off and a brown solid was recovered, which was taken up in ethanol to remove the insoluble matter.

After evaporating off the ethanol, the solid was purified on a column of silica. 504 mg of a dark brown solid corresponding to the expected product were thus isolated.

Analysis by Mass Spectrometry

The expected cation $[C_{19}H_{25}N_6O]+$ was mainly detected at m/z, ESP+=353.

Example 2

Synthesis of 2-[(3-{[(1E)-2-amino-3-chloro-5-methyl-4-oxocyclohexa-2,5-dien-1-ylidene]amino}pyrazolo[1,5-a]pyridin-2-yl)amino]-N,N,N-trimethylethanaminium chloride

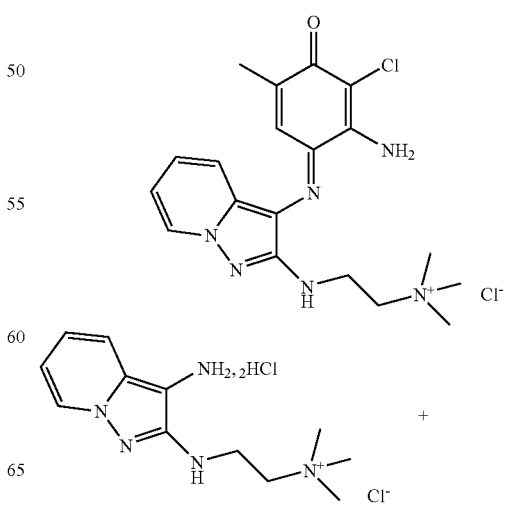

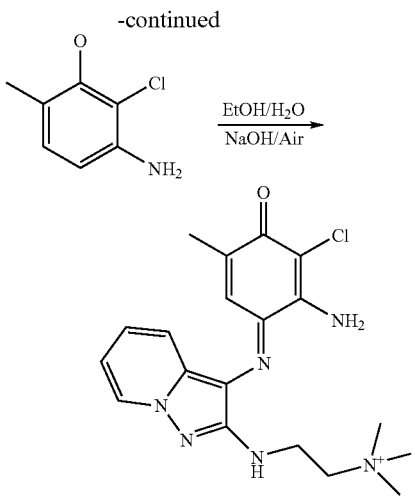

5.83 mmol of 2-[(3-aminopyrazolo[1,5-a]pyridin-2-yl)amino]-N,N,N-trimethylethanaminium chloride hydrochloride dissolved in 30 ml of water were placed in a 100 ml one-necked round-bottomed flask. 5.83 mmol of 3-amino-2-chloro-6-methylphenol and then 17.5 mmol of sodium carbonate were added to this solution.

The reaction medium, which was initially pale blue, turned dark blue. The reaction took place at room temperature overnight. After leaving overnight and evaporating off the solvent, a dark brown solid was isolated.

After drying in a desiccator under vacuum for 12 hours, 2.46 g of expected compound were obtained.

Analysis by Mass Spectrometry

The expected cation $[C_{19}H_{24}ClN_6O]+$ was mainly detected at m/z, ESP+=387.

Example 3

Synthesis of 2-[(3-{[(1E)-2-amino-5-(2-hydroxyethoxy)-4-iminocyclohexa-2,5-dien-1-ylidene]amino}pyrazolo[1,5-a]pyridin-2-yl)amino]-N,N,N-trimethylethanaminium chloride hydrochloride

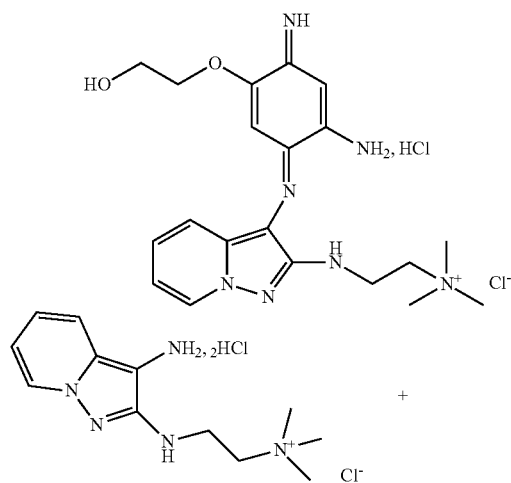

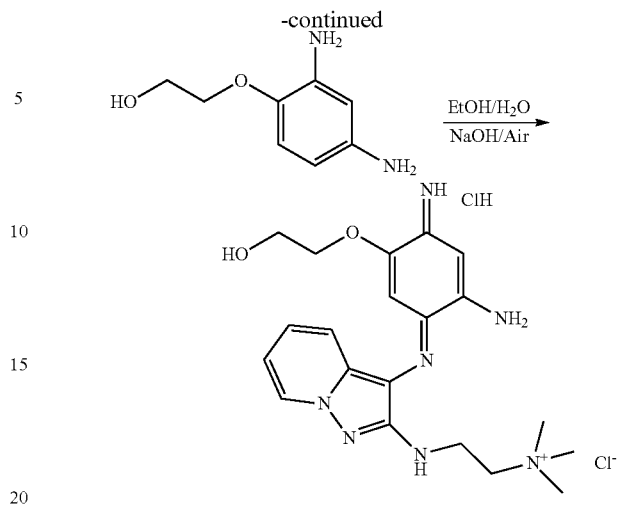

8.75 mmol of 2-[(3-aminopyrazolo[1,5-a]pyridin-2-yl)amino]-N,N,N-trimethylethanaminium chloride dihydrochloride were dissolved in 50 ml of ethanol and 4 ml of water.

8.75 mmol of 2-(2,4-diaminophenoxy)ethanol were added to this solution, followed by 43.75 mmol of 20% aqueous ammonia solution.

The reaction took place at room temperature overnight. After leaving overnight and evaporating off the solvents, the dark brown solid formed was isolated by filtration.

The dark brown powder obtained was dried in a desiccator under vacuum for 12 hours to obtain 2.97 g of expected compound.

Analysis by Mass Spectrometry

The expected cation $[C_{20}H_{28}N_7O_2]+$ was mainly detected at m/z, ESP+=398.

Example 4

Synthesis of 1-{2-[(3-{[(1E)-2-amino-5-methyl-4-oxocyclohexa-2,5-dien-1-ylidene]amino}pyrazolo[1,5-a]pyridin-2-yl)amino]ethyl}-1-methylpiperidinium chloride

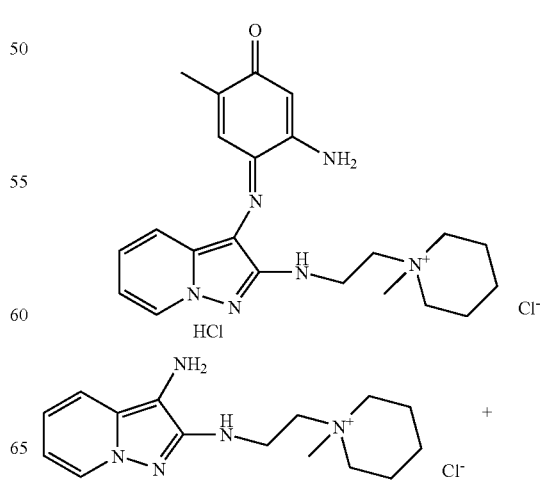

-continued

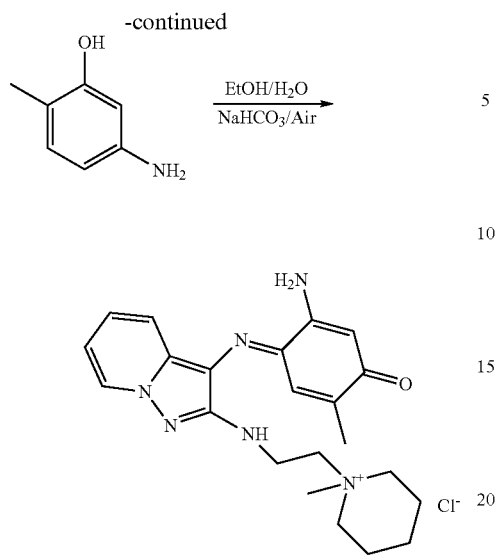

5.77 mmol of 1-{2-[(3-aminopyrazolo[1,5-a]pyridin-2-yl)amino]ethyl}-1-methylpiperidinium chloride hydrochloride and 5.77 mmol of 3-amino-6-methylphenol in 20 ml of ethanol were placed in a 100 ml one-necked round-bottomed flask.

A solution of 28.87 mmol of sodium hydrogen carbonate in 8 ml of water was added slowly to this mixture.

After reacting for 24 hours at room temperature, the solvent was removed by evaporation and the residue was chromatographed on a column of silica (eluent: dichloromethane (80), methanol (15), aqueous ammonia (5)).

This purification allowed isolation, after evaporating off the solvents, of 1.24 g of expected compound in the form of a brown powder.

Analysis by Mass Spectrometry

The expected cation $[C_{22}H_{29}N_6O]+$ was mainly detected at m/z, ESP+=393.

Example 5

Synthesis of 1-{2-[(3-{[(1E)-2-amino-3-chloro-5-methyl-4-oxocyclohexa-2,5-dien-1-ylidene]amino}pyrazolo[1,5-a]pyridin-2-yl)amino]ethyl}-1-methylpiperidinium chloride

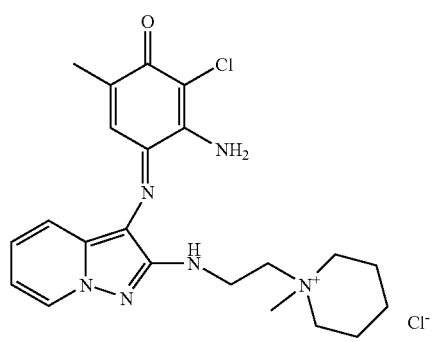

-continued

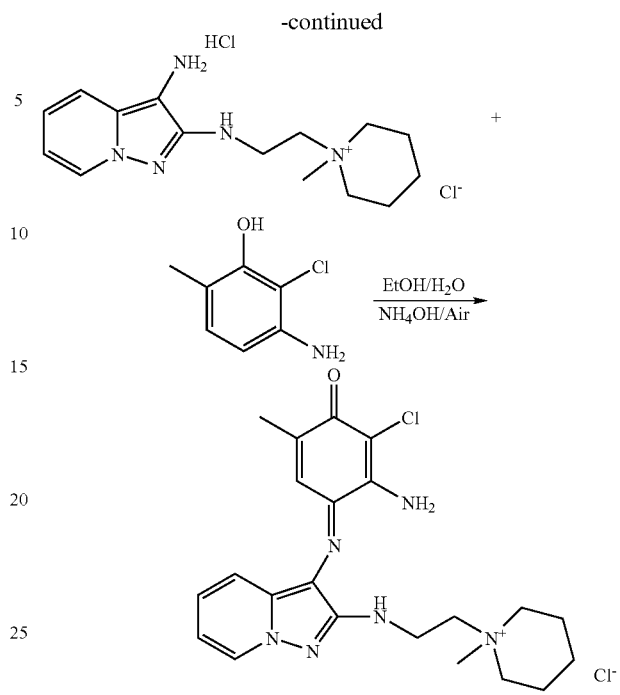

0.577 mmol of 1-{2-[(3-aminopyrazolo[1,5-a]pyridin-2-yl)amino]ethyl}-1-methylpiperidinium chloride hydrochloride and 0.577 mmol of 3-amino-2-chloro-6-methylphenol in 10 ml of water and 2 ml of ethanol were placed in a 100 ml one-necked round-bottomed flask.

10 ml of 20% aqueous ammonia solution were added to this mixture. After stirring for 24 hours, the reaction medium was evaporated to give a brown solid.

This solid was washed with a minimum amount of acetone and a minimum amount of diethyl ether. After drying under vacuum at 50° C., 231 mg of a brown solid corresponding to the expected product were obtained.

Analysis by Mass Spectrometry

The expected cation $[C_{22}H_{28}ClN_6O]+$ was mainly detected at m/z, ESP+=427.

Example 6

Synthesis of 4-{2-[(3-{[(1E)-2-amino-5-(2-hydroxyethoxy)-4-oxocyclohexa-2,5-dien-1-ylidene]amino}pyrazolo[1,5-a]pyridin-2-yl)amino]ethyl}-1,1-dimethylpiperazin-1-ium chloride

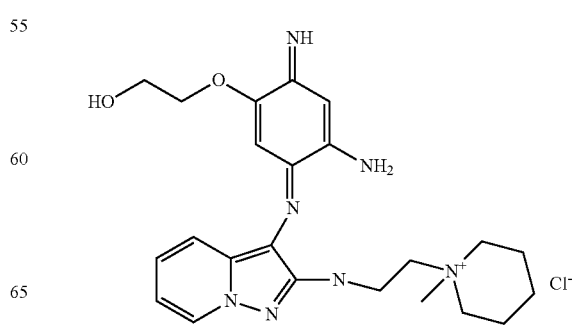

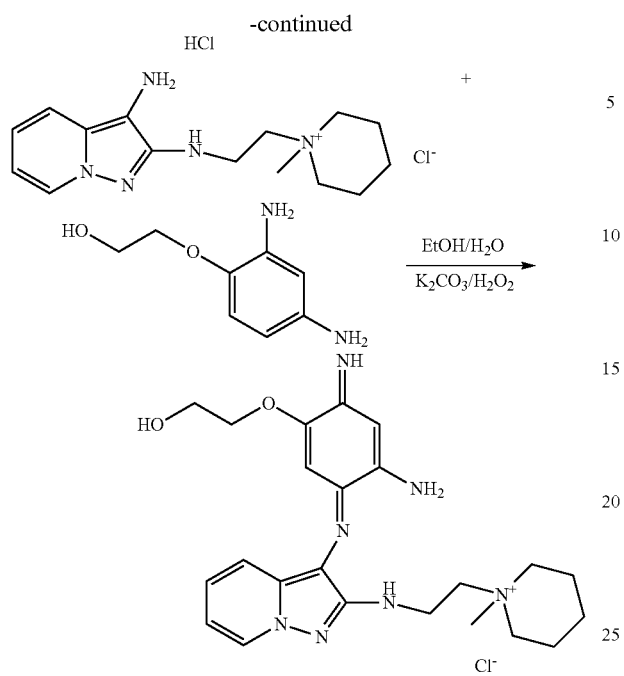

0.577 mmol of 1-{2-[(3-aminopyrazolo[1,5-a]pyridin-2-yl)amino]ethyl}-1-methylpiperidinium chloride hydrochloride and 0.577 mmol of 5-amino-2-(2-hydroxyethoxy)phenol in 10 ml of water and 2 ml of ethanol were placed in a 100 ml one-necked round-bottomed flask.

10 ml of 20% aqueous ammonia solution were added to this mixture. After stirring for 24 hours, the dark brown solid formed was isolated by filtration, washed with a minimum amount of acetone and dried under vacuum at 40° C. for 6 hours. 249 mg of a brown solid corresponding to the expected product were thus isolated.

Analysis by Mass Spectrometry

The expected cation $[C_{23}H_{32}N_7O_2]+$ was mainly detected at m/z, ESP+=438.

Example 7

Synthesis of 1-{2-[(3-{[(1E)-2-amino-5-(2-hydroxyethoxy)-4-iminocyclohexa-2,5-dien-1-ylidene]amino}pyrazolo[1,5-a]pyridin-2-yl)oxy]ethyl}-1-methylpiperidinium chloride

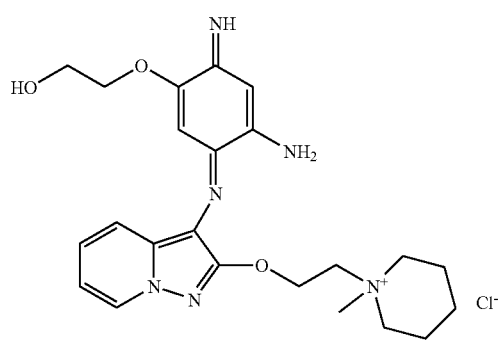

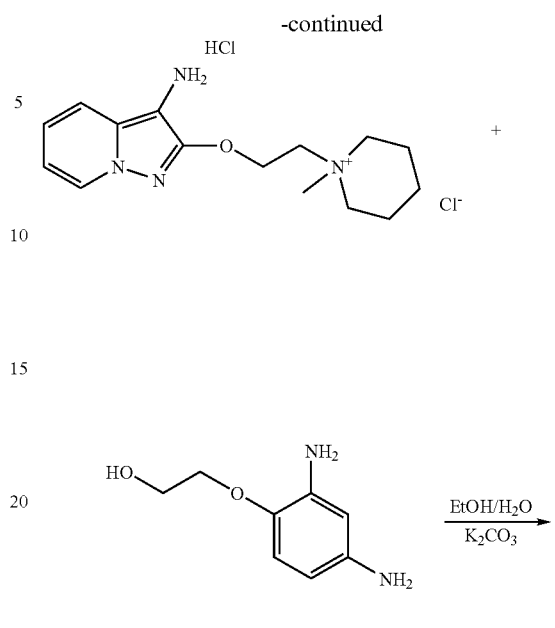

2.87 mmol of 1-{2-[(3-aminopyrazolo[1,5-a]pyridin-2-yl)oxy]ethyl}-1-methylpiperidinium chloride hydrochloride and 2.87 mmol of 5-amino-2-(2-hydroxyethoxy)phenol in 25 ml of ethanol were placed in a 100 ml one-necked round-bottomed flask.

A solution of 11.48 mmol of potassium carbonate in 2 ml of water was added to this mixture, followed, with stirring, by addition of 0.1 ml of 9-volumes aqueous hydrogen peroxide solution, and stirring was continued for 24 hours.

The dark brown solid formed was isolated by filtration, washed with a minimum amount of acetone and dried under vacuum at 40° C. for 6 hours. 554.3 mg of a brown solid corresponding to the expected product were thus isolated.

Analysis by Mass Spectrometry

The expected cation $C_{23}H_{31}N_6O_3$ of mass 439 was mainly detected.

Example 8

Synthesis of 4-[3-({(1E)-2-[(2-hydroxyethyl)amino]-5-methyl-4-oxocyclohexa-2,5-dien-1-ylidene}amino)pyrazolo[1,5-a]pyridin-2-yl]-1,1-dimethylpiperazin-1-ium chloride

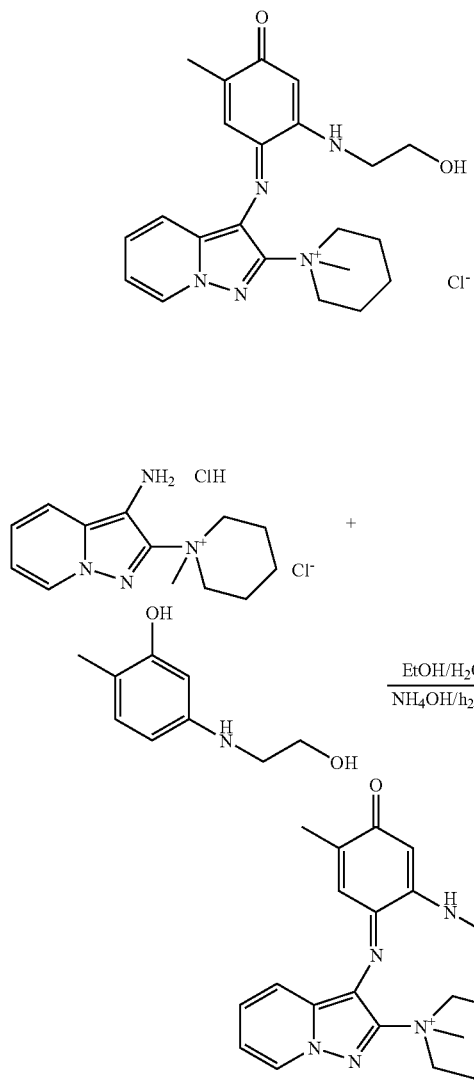

5 mmol of 4-(3-aminopyrazolo[1,5-a]pyridin-2-yl)-1,1-dimethylpiperazin-1-ium hydrochloride dissolved in 2 ml of ethanol and 8 ml of water were placed in a 100 ml one-necked round-bottomed flask.

5 mmol of 5-[(2-hydroxyethyl)amino]-2-methylphenol, 1 ml of 20% aqueous ammonia so as to obtain a pH of 9.5, and 1 ml of aqueous hydrogen peroxide solution as oxidizing agent were added to this solution.

The reaction medium (violet-blue solution) was stirred for 30 minutes at room temperature and the expected product was monitored by LC/MS spectrometry.

Analysis by Mass Spectrometry

The expected cation $C_{22}H_{29}N_6O_2$ was mainly detected.

Example 9

Synthesis of 1-(2-{[3-({(1E)-2-[(2-hydroxyethyl)amino]-5-methyl-4-oxocyclohexa-2,5-dien-1-ylidene}amino)pyrazolo[1,5-a]pyridin-2-yl]amino}ethyl)-3-methyl-1H-imidazol-3-ium chloride

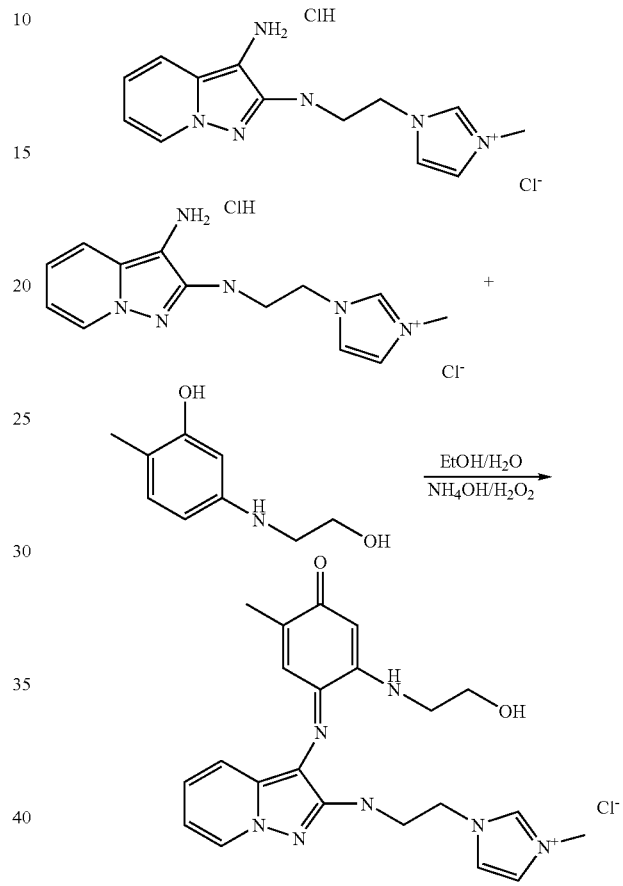

5 mmol of 1-{2-[(3-aminopyrazolo[1,5-a]pyridin-2-yl)amino]ethyl}-3-methyl-1H-imidazol-3-ium chloride hydrochloride dissolved in 2 ml of ethanol and 8 ml of water were placed in a 100 ml one-necked round-bottomed flask.

5 mmol of 5-[(2-hydroxyethyl)amino]-2-methylphenol, 1 ml of 20% aqueous ammonia so as to obtain a pH of 9.5, and 1 ml of aqueous hydrogen peroxide solution as oxidizing agent were added to this solution.

The reaction medium (blue solution) was stirred for 30 minutes at room temperature, and the expected product was monitored by LC/MS spectrometry.

Analysis by Mass Spectrometry

The expected cation $C_{22}H_{26}N_7O_2$ was mainly detected.

Examples of Dyeing

Examples 1 to 7 of Dyeing in Acidic Medium

The following dye compositions were prepared:

| Dye Example      | $10^{-3}$ mol |
|------------------|---------------|
| Dye support (1)  | (*)           |

-continued

| | |
|---|---|
| Demineralized water qs | 100 g |

Example 1

[chemical structure]

Example 2

[chemical structure]

Example 3

[chemical structure]

Example 4

[chemical structure]

Example 5

[chemical structure]

Example 6

[chemical structure]

Example 7

[chemical structure]

(*): dye support (1) pH 7
dye support (1) pH 7:

| | |
|---|---|
| 96° ethyl alcohol | 20.8 g |
| Pentasodium salt of diethylenetriaminepentaacetic acid as an aqueous 40% solution | 0.48 g AM |
| $C_8$-$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

Each mixture obtained was applied to locks of grey hair comprising 90% white hairs. After a leave-on time of 30 minutes, the locks were rinsed, washed with a standard shampoo, rinsed again and then dried.

The shades obtained were given in the table below:

| Example | 1 | 2 | 3 | 4 |
|---|---|---|---|---|
| Shade observed | Bright violet | Bright violet-blue | Bright blue | Bright violet |
| Example | 5 | 6 | 7 | |
| Shade observed | Bright violet-blue | Bright blue | Bright red-violet | |

For the dyeing in oxidizing media: at the time of use, each of the compositions described above was mixed with an equal weight of 20-volumes aqueous hydrogen peroxide solution (6% by weight). A final pH of 7 was obtained.

The shades obtained were given in the table below:

| Example | 1 | 2 | 3 | 4 |
|---|---|---|---|---|
| Shade observed | Bright blue-violet | Bright blue-violet | Bright blue | Bright violet |

-continued

| Example | 5 | 6 | 7 |
|---|---|---|---|
| Shade observed | Bright blue-violet | Bright blue | Bright red-violet |

Examples 8 to 14 of Dyeing in Basic Medium
The following dye compositions are prepared:

| Dye Example | $10^{-3}$ mol |
|---|---|
| Dye support (2) | (*) |
| Demineralized water qs | 100 g |

Example 1

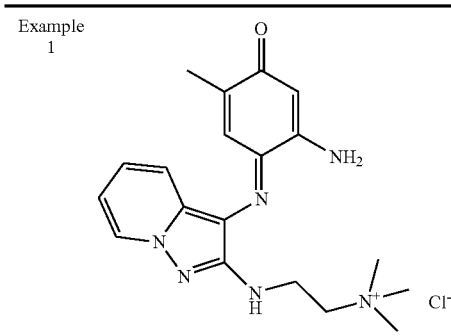

Example 2

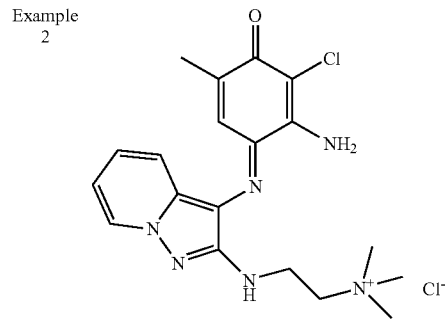

Example 3

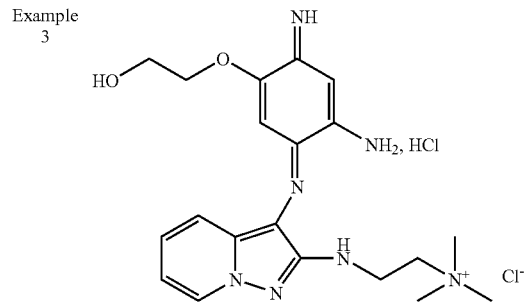

Example 4

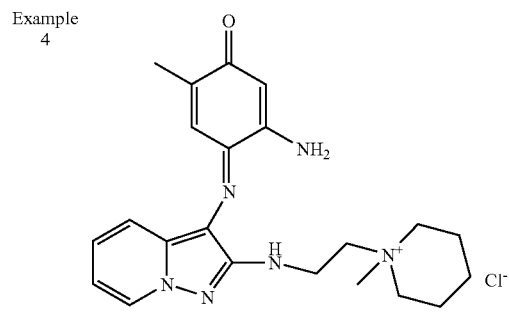

Example 5

[structure]

Example 6

[structure]

Example 7

[structure]

(*): dye support (2) pH 9.5
dye support (2) pH 9.5:

| 96° ethyl alcohol | 20.8 g |
|---|---|
| Pentasodium salt of diethylenetriaminepentaacetic acid as an aqueous 40% solution | 0.48 g AM |
| $C_8$-$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

Each mixture obtained was applied to locks of grey hair comprising 90% white hairs. After a leave-on time of 30 minutes, the locks were rinsed, washed with standard shampoo, rinsed again and then dried.

The shades obtained are given in the following table:

| Example | 1 | 2 | 3 | 4 |
|---|---|---|---|---|
| Shade observed | Violet | Bright blue | Bright blue-green | Bright violet |

| Example | 5 | 6 | 7 |
|---|---|---|---|
| Shade observed | Bright blue | Bright blue-green | Red-violet |

For the oxidizing media: at the time of use, each of the compositions described above was mixed with an equal weight of 20-volumes aqueous hydrogen peroxide solution (6% by weight). A final pH of 9.5 was obtained.

The shades obtained were given in the table below:

| Example | 1 | 2 | 3 | 4 |
|---|---|---|---|---|
| Shade observed | Violet | Blue | Blue-green | Violet |

| Example | 5 | 6 | 7 |
|---|---|---|---|
| Shade observed | Blue | Bright blue-green | Bright red-violet |

What is claimed is:

1. At least one compound chosen from leuco form compounds of formula (I), dyes of azomethine type comprising a pyrazolopyridine unit of formula (II), mesomeric forms, isomeric forms and tautomeric forms thereof, acid-addition salts thereof and solvates thereof:

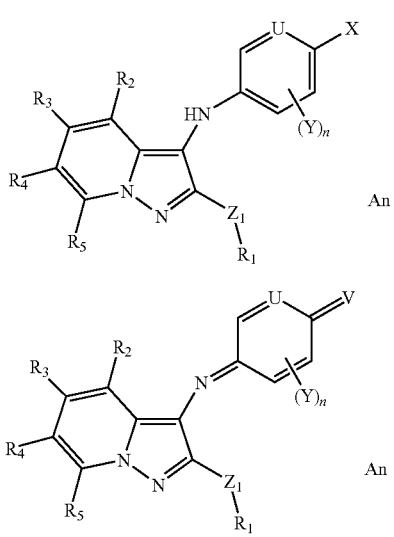

in which:

$Z_1$ represents:

a single covalent bond;

a divalent radical chosen from:

an oxygen atom; and $NR_6(R_7)p$, with p=0 or 1;

when p is equal to 0, $R_6$ represents a hydrogen atom or a $C_1$-$C_6$ alkyl, or $R_6$ with $R_1$ form, together with the nitrogen atom to which they are attached, a substituted or unsubstituted, saturated or unsaturated, aromatic or non-aromatic 5- to 8-membered heterocycle optionally comprising at least one additional radical chosen from N, O, S, $SO_2$ and —CO—, wherein the heterocycle can be cationic and/or substituted with at least one cationic or non-cationic radical;

when p is equal to 1, $NR_6R_7$ is a cationic radical in which $R_6$ and $R_7$ independently represent an alkyl radical;

$Z_1$ can also represent a divalent radical —S—, —SO—, or —$SO_2$— when $R_1$ is a methyl;

$R_1$ represents:

a hydrogen;

an optionally substituted $C_1$-$C_{10}$ alkyl, optionally interrupted with at least one radical chosen from O, N, Si, S, SO and $SO_2$;

a $C_1$-$C_{10}$ alkyl substituted and/or interrupted with a cationic radical;

a halogen;

a radical $SO_3H$; or a substituted or unsubstituted, saturated, unsaturated or aromatic 5- to 8-membered ring, optionally comprising at least one radical chosen from N, O, S, $SO_2$ and —CO—, the ring can be cationic and/or substituted with a cationic radical;

when $Z_1$ represents a covalent bond, $R_1$ can represent:

an optionally substituted $C_1$-$C_6$ alkylcarbonyl; or a radical —O—CO—R, —CO—O—R, —NR—CO—R' or —CO—NRR' in which R and R' independently represent a hydrogen atom or an optionally substituted $C_1$-$C_6$ alkyl;

$R_2$, $R_3$, $R_4$ and $R_5$, which may be identical or different, represent:

a hydrogen atom;

a hydroxyl;

a $C_1$-$C_6$ alkoxy;

a $C_1$-$C_6$ alkylthio;

an amino;

a monoalkylamino;

a $C_1$-$C_6$ dialkylamino in which the alkyl can form, with the nitrogen atom to which they are attached, a saturated or unsaturated, aromatic or non-aromatic 5- to 8-membered heterocycle optionally comprising at least one additional entity chosen from N, O, S, $SO_2$ and CO, the heterocycle can be cationic and/or substituted with a cationic radical;

an optionally substituted $C_1$-$C_6$ alkylcarbonyl;

a —O—CO—R, —CO—O—R, —NR—CO—R' or —CO—NRR' in which R and R' independently represent a hydrogen atom or an optionally substituted $C_1$-$C_6$ alkyl;

a halogen;

a $NHSO_3H$;

an optionally substituted $C_1$-$C_4$ alkyl;

a saturated, unsaturated or aromatic, optionally substituted carbon-based ring; or two adjacent $R_2$, $R_3$, $R_4$ and $R_5$ may form, together with the carbons they are attached, a saturated or unsaturated 5- or 6-membered ring;

An represents at least one anion that ensures the electronegativity of the compounds of formulae (I) and (II);

provided that at least one of the groups $Z_1$ and $R_1$ represents a cationic radical;

n is an integer ranging from 0 to 3;

U represents CR or N;

R represents:

a hydrogen atom;

a $C_1$-$C_4$ alkyl optionally substituted with a hydroxyl;

a $C_1$-$C_4$ alkoxy optionally substituted with a hydroxyl; or a (di)($C_1$-$C_4$)alkylamino in which the alkyl part is optionally substituted with a hydroxyl;

X represents:

a hydroxyl; or a group $NR'_1R''_1$, wherein $R'_1$ and $R''_1$ are chosen independently from a hydrogen atom; a $C_1$-$C_6$ alkyl optionally substituted with at least one radical chosen from a hydroxyl, ($C_1$-$C_2$)alkoxy, amino, and (di)($C_1$-$C_2$)alkylamino; and a phenyl radical optionally substituted with at least one radical chosen from hydroxyl, amino and $(C_1-C_2)$alkoxy;

when $R'_1$ and $R''_1$ are other than a hydrogen, $R'_1$ and $R''_1$ can form, together with the nitrogen atom to which they are attached, a saturated or unsaturated 5- to 7-membered heterocycle optionally comprising at least one additional heteroatom chosen from an oxygen and nitrogen atom, and optionally substituted with at least one entity chosen from a halogen atom, an amino, (di)($C_1-C_4$)alkylamino, hydroxyl, carboxyl, carboxamido, ($C_1-C_2$) alkoxy and $C_1-C_4$ alkyl, optionally substituted with at least one radical chosen from hydroxyl, amino, (di)alkylamino, alkoxy, carboxyl and sulfonyl radical;

when X represents a group $NHR'_1$ and when U represents a group CR in which R denotes an alkoxy, X and U may form a 6-membered ring of morpholine type, optionally substituted with at least one $C_1-C_4$ alkyl;

V represents:

an oxygen atom; or a group $NR'_1$, wherein $R'_1$ is chosen from a hydrogen atom; a $C_1-C_6$ alkyl optionally substituted with at least one radical chosen from hydroxyl, $(C_1-C_2)$alkoxy, and amino and (di)($C_1-C_2$)alkylamino; and a phenyl radical optionally substituted with at least one radical chosen from hydroxyl, amino and $(C_1-C_2)$alkoxy;

when V represents a group $NR'_1$ and when U represents a group CR in which R denotes an alkoxy, V and U can form a 6-membered ring of morpholine type, optionally substituted with at least one $C_1-C_4$ alkyl;

Y, which may be identical or different, represent:

a hydroxyl;

a $C_1-C_4$ alkyl;

a $C_1-C_4$ hydroxyalkyl;

a halogen;

an oxygen atom substituted with a radical chosen from a $C_1-C_4$ alkyl, an aryl radical and a heteroaryl radical, optionally substituted with at least one hydroxyl; or a group $NR'_2R'_3$, $R'_2$ and $R'_3$, which may be identical or different, are chosen from:

a hydrogen atom;

a $C_1-C_4$ alkylcarbonyl optionally substituted with a quaternary ammonium group, or with a cationic or non-cationic nitrogenous heterocycle optionally substituted with at least one $C_1-C_4$ alkyl;

an aminocarbonyl;

a $C_1-C_6$ alkyl optionally substituted with at least one radical chosen from hydroxyl, ($C_1-C_2$)alkoxy, amino and (di)($C_1-C_2$)alkylamino; and a phenyl optionally substituted with at least one radical chosen from hydroxyl, amino and $(C_1-C_2)$alkoxy; or $R'_2$ and $R'_3$ can form, together with the nitrogen atom to which they are attached, a saturated or unsaturated, 5- to 7-membered heterocycle optionally comprising at least one additional heteroatom chosen from oxygen and nitrogen atoms, and optionally substituted with at least one radical chosen from a halogen, amino, (di)($C_1-C_4$) alkylamino, hydroxyl, carboxyl, (di)alkylcarboxamido, $(C_1-C_2)$alkoxy and $C_1-C_4$, optionally substituted with at least one radical chosen from hydroxyl, amino, (di)alkylamino, alkoxy, carboxyl and sulfonyl; or two radicals Y borne by two adjacent carbon atoms may form, together with the carbon atoms to which they are attached, a saturated or unsaturated, aromatic or non-aromatic, 5- to 6-membered cyclic or heterocyclic optionally substituted with at least one $C_1-C_4$ alkyl.

2. The at least one compound according to claim 1, wherein Y represents a group $NR'_2R'_3$, in which $R'_2$ and $R'_3$, which may be identical or different, are chosen from a $C_1-C_4$ alkylcarbonyl optionally substituted with a quaternary ammonium group chosen from trialkylammonium, or with a cationic or non-cationic nitrogenous heterocycle chosen from imidazole, thiazole, pyridine, piperidine, pyrrolidine, pyrimidine, pyrazine, imidazolium, pyridinium, thiazolium, pyrrolidinium, piperidinium and pyrimidinium, optionally substituted with at least one $C_1-C_4$ alkyl.

3. The at least one compound according to claim 1, wherein two radicals Y borne by two adjacent carbon atoms form, together with the carbon atoms to which they are attached, a saturated or unsaturated, aromatic or non-aromatic, 5- to 6-membered cyclic or heterocyclic group chosen from benzene, pyrrole, pyrrolidine, pyrazole, furan, pyrrolidine, morpholine or imidazole, optionally substituted with at least one $C_1-C_4$ alkyl.

4. The at least one compound according to claim 1, in which $Z_1$ represents a single covalent bond, a radical —O—, a radical $NR_6$, wherein $R_6$ represents a hydrogen atom or an alkyl, or $R_6$ forms with $R_1$ a heterocycle which is cationic and/or substituted with a cationic radical.

5. The at least one compound according to claim 1, in which $R_1$ represents a hydrogen atom or an alkyl optionally interrupted or substituted with a cationic radical.

6. The at least one compound according to claim 1, in which $R_2$, $R_3$, $R_4$ and $R_5$ independently represent a hydrogen atom or a $C_1-C_4$ alkyl optionally substituted with at least one radical chosen from methyl, ethyl, hydroxyethyl, aminoethyl, propyl and butyl.

7. The at least one compound according to claim 1, in which U represents CR or N, and R represents a hydrogen atom, a $C_1-C_4$ alkyl, a $C_1-C_4$ alkoxy optionally substituted with at least one radical chosen from a hydroxyl, or a (di)($C_1$-$C_4$)alkylamino in which the alkyl is optionally substituted with at least one hydroxyl.

8. The at least one compound according to claim 1, in which X represents a hydroxyl; or a group $NR'_1R''_1$ wherein $R'_1$ and $R''_1$ independently chosen from a hydrogen atom, and a $C_1-C_6$ alkyl optionally substituted with at least one hydroxyl, or $R'_1$ and $R''_1$, together with the nitrogen to which they are attached, form a heterocycle.

9. The at least one compound according to claim 1, in which V represents an oxygen atom; or a group $NR'_1$ in which $R'_1$ represents a hydrogen atom or a $C_1-C_6$ alkyloptionally substituted with at least one hydroxyl.

10. The at least one compound according to claim 1, in which X and U, or, V and U, form a 6-membered ring of morpholine type, optionally substituted with at least one $C_1-C_4$ alkyl.

11. The at least one compound according to claim 1, in which Y, which may be identical or different, represent a hydroxyl; a $C_1-C_4$ alkyl; a halogen; an oxygen atom substituted with a $C_1-C_4$ alkyl, optionally substituted with at least one hydroxyl; or a group $NR'_2R'_3$, wherein $R'_2$ and $R'_3$, which may be identical or different, are chosen from a hydrogen atom, a $C_1-C_4$ alkylcarbonyl, an aminocarbonyl, and a $C_1-C_6$ alkyl optionally substituted with at least one hydroxyl, or $R'_2$ and $R'_3$ form, together with the nitrogen atom to which they are attached, a saturated 5- to 7-membered heterocycle.

12. The at least one compound according to claim 1 chosen from compounds of formulae (IIa) and (IIb):

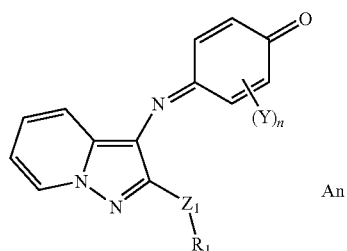 (IIa)

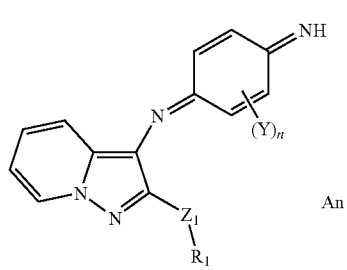 (IIb)

in which $Z_1$ represents:

a single covalent bond; or a divalent radical chosen from:
  an oxygen atom; and
  a $NR_6(R_7)p$, with p=0 or 1;

when p is equal to 0, $R_6$ represents a hydrogen atom or a $C_1$-$C_6$ alkyl, or $R_6$ with $R_1$ form, together with the nitrogen atom to which they are attached, a substituted or unsubstituted, saturated or unsaturated, aromatic or non-aromatic 5- to 8-membered heterocycle optionally comprising at least one additional radical chosen from N, O, S, $SO_2$ and —CO—, wherein the heterocycle can be cationic and/or substituted with at least one cationic or non-cationic radical;

when p is equal to 1, $NR_6R_7$ is a cationic radical in which $R_6$ and $R_7$ independently represent an alkyl radical;

$Z_1$ can also represent a divalent radical —S—, —SO—, or —$SO_2$— when $R_1$ is a methyl radical;

$R_1$ represents:

a hydrogen;

an optionally substituted $C_1$-$C_{10}$ alkyl radical, optionally interrupted with at least one radical chosen from O, N, Si, S, SO and $SO_2$;

a $C_1$-$C_{10}$ alkyl radical substituted and/or interrupted with a cationic radical;

a halogen;

a radical $SO_3H$; or a substituted or unsubstituted, saturated, unsaturated or aromatic 5- to 8-membered ring, optionally comprising at least one radical chosen from N, O, S, $SO_2$ and —CO—, the ring can be cationic and/or substituted with a cationic radical;

when $Z_1$ represents a covalent bond, $R_1$ can represent:

an optionally substituted $C_1$-$C_6$ alkylcarbonyl; or a —O—CO—R, —CO—O—R, —NR—CO—R' or —CO—NRR' in which R and R' independently represent a hydrogen atom or an optionally substituted $C_1$-$C_6$ alkyl;

An represents at least one anion that ensures the electronegativity of the compounds of formulae (IIa) and (IIb);

provided that at least one of the groups $Z_1$ and $R_1$ represents a cationic radical;

n is an integer ranging from 0 to 3;

Y, which may be identical or different, represent:

a hydroxyl;

a $C_1$-$C_4$ alkyl;

a $C_1$-$C_4$ hydroxyalkyl;

a halogen;

an oxygen atom substituted with a radical chosen from a $C_1$-$C_4$ alkyl, an aryl radical and a heteroaryl radical, optionally substituted with at least one hydroxyl; or a group $NR'_2R'_3$, $R'_2$ and $R'_3$, which may be identical or different, are chosen from:

a hydrogen atom;

a $C_1$-$C_4$ alkylcarbonyl optionally substituted with a quaternary ammonium group, or with a cationic or non-cationic nitrogenous heterocycle optionally substituted with at least one $C_1$-$C_4$ alkyl;

an aminocarbonyl;

a $C_1$-$C_6$ alkyl optionally substituted with at least one radical chosen from hydroxyl, ($C_1$-$C_2$)alkoxy, amino and (di)($C_1$-$C_2$)alkylamino; and a phenyl radical optionally substituted with at least one radical chosen from hydroxyl, amino and ($C_1$-$C_2$) alkoxy; or $R'_2$ and $R'_3$ can form, together with the nitrogen atom to which they are attached, a saturated or unsaturated, 5- to 7-membered heterocycle optionally comprising at least one additional heteroatom chosen from an oxygen and nitrogen atom, and optionally substituted with at least one radical chosen from a halogen, amino, (di)($C_1$-$C_4$)alkylamino, hydroxyl, carboxyl, (di)alkylcarboxamido, ($C_1$-$C_2$)alkoxy and $C_1$-$C_4$, optionally substituted with at least one radical chosen from hydroxyl, amino, (di)alkylamino, alkoxy, carboxyl and sulfonyl; or two radicals Y borne by two adjacent carbon atoms may form, together with the carbon atoms to which they are attached, a saturated or unsaturated, aromatic or non-aromatic, 5- to 6-membered cyclic or heterocyclic optionally substituted with at least one $C_1$-$C_4$ alkyl.

13. The at least one compound according to claim 12, in which $Z_1$ is chosen from an oxygen atom and a group $NR_6$, $R_1$ is an alkyl radical optionally interrupted or substituted with a quaternary ammonium, and when $Z_1$ is $NR_6$, $R_1$ can form with $R_6$ a piperazinium ring, n is 0, 1 or 2, and Y is chosen from hydroxyl, alkyl, hydroxyalkoxy and halogen.

14. The at least one compound according to claim 13, wherein the quaternary ammonium is imidazolium, trialkylammonium or pyrrolidinium.

15. A composition for dyeing keratin fibers, comprising, in a suitable dyeing medium, at least one compound chosen from leuco form compounds of formula (I), dyes of azomethine type comprising a pyrazolopyridine unit of formula (II), mesomeric, isomeric and tautomeric forms thereof, acid-addition salts thereof and solvates thereof:

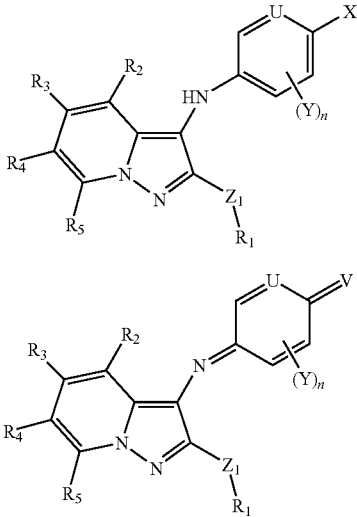

in which:

$Z_1$ represents:

a single covalent bond;

a divalent radical chosen from:
  an oxygen atom; and
  a $NR_6(R_7)p$, with p=0 or 1;

when p is equal to 0, $R_6$ represents a hydrogen atom or a $C_1$-$C_6$ alkyl, or $R_6$ with $R_1$ form, together with the nitrogen atom to which they are attached, a substituted or unsubstituted, saturated or unsaturated, aromatic or non-aromatic 5- to 8-membered heterocycle optionally comprising at least one additional radical chosen from N, O, S, $SO_2$ and —CO—, wherein the heterocycle can be cationic and/or substituted with at least one cationic or non-cationic radical;

when p is equal to 1, $NR_6R_7$ is a cationic radical in which $R_6$ and $R_7$ independently represent an alkyl radical;

$Z_1$ can also represent a divalent radical —S—, —SO—, or —$SO_2$— when $R_1$ is a methyl;

$R_1$ represents:

a hydrogen;

an optionally substituted $C_1$-$C_{10}$ alkyl, optionally interrupted with at least one radical chosen from O, N, Si, S, SO and $SO_2$;

a $C_1$-$C_{10}$ alkyl substituted and/or interrupted with a cationic radical;

a halogen;

a radical $SO_3H$; or a substituted or unsubstituted, saturated, unsaturated or aromatic 5- to 8-membered ring, optionally comprising at least one radical chosen from N, O, S, $SO_2$ and —CO—, the ring can be cationic and/or substituted with a cationic radical;

when $Z_1$ represents a covalent bond, $R_1$ can represent:

an optionally substituted $C_1$-$C_6$ alkylcarbonyl;

a radical —O—CO—R, —CO—O—R, —NR—CO—R' or —CO—NRR' in which R and R' independently represent a hydrogen atom or an optionally substituted $C_1$-$C_6$ alkyl;

$R_2$, $R_3$, $R_4$ and $R_5$, which may be identical or different, represent:

a hydrogen atom;

a hydroxyl;

a $C_1$-$C_6$ alkoxy;

a $C_1$-$C_6$ alkylthio;

an amino;

a monoalkylamino;

a $C_1$-$C_6$ dialkylamino in which the alkyl can form, with the nitrogen atom to which they are attached, a saturated or unsaturated, aromatic or non-aromatic 5- to 8-membered heterocycle optionally comprising at least one additional radical chosen from N, O, S, $SO_2$ and CO, the heterocycle can be cationic and/or substituted with a cationic radical;

an optionally substituted $C_1$-$C_6$ alkylcarbonyl;

a —O—CO—R, —CO—O—R, —NR—CO—R' or —CO—NRR' in which R and R' independently represent a hydrogen atom or an optionally substituted $C_1$-$C_6$ alkyl;

a halogen;

a $NHSO_3H$;

an optionally substituted $C_1$-$C_4$ alkyl;

a saturated, unsaturated or aromatic, optionally substituted carbon-based ring; or two adjacent $R_2$, $R_3$, $R_4$ and $R_5$ may form, together with the carbons they are attached, a saturated or unsaturated 5- or 6-membered ring;

An represents at least one anion that ensures the electronegativity of the compounds of formulae (I) and (II);

provided that at least one of the groups $Z_1$ and $R_1$ represents a cationic radical;

n is an integer ranging from 0 to 3;

U represents CR or N;

R represents:

a hydrogen atom;

a $C_1$-$C_4$ alkyl optionally substituted with a hydroxyl;

a $C_1$-$C_4$ alkoxy optionally substituted with a hydroxyl; or a (di)($C_1$-$C_4$)alkylamino in which the alkyl part is optionally substituted with a hydroxyl;

X represents:

a hydroxyl; or a group $NR'_1R''_1$, wherein $R'_1$ and $R''_1$ are chosen independently from a hydrogen atom; a $C_1$-$C_6$ alkyl optionally substituted with at least one radical chosen from a hydroxyl, ($C_1$-$C_2$)alkoxy, amino, and (di)($C_1$-$C_2$)alkylamino; and a phenyl radical optionally substituted with at least one radical chosen from hydroxyl, amino and ($C_1$-$C_2$)alkoxy;

when $R'_1$ and $R''_1$ are other than a hydrogen, $R'_1$ and $R''_1$ can form, together with the nitrogen atom to which they are attached, a saturated or unsaturated 5- to 7-membered heterocycle optionally comprising at least one additional heteroatom chosen from an oxygen and nitrogen atom, and optionally substituted with at least one radical chosen from a halogen atom, an amino, (di)($C_1$-$C_4$)alkylamino, hydroxyl, carboxyl, carboxamido, ($C_1$-$C_2$) alkoxy and $C_1$-$C_4$ alkyl, optionally substituted with at least one radical chosen from hydroxyl, amino, (di)alkylamino, alkoxy, carboxyl and sulfonyl radical;

when X represents a group $NHR'_1$ and when U represents a group CR in which R denotes an alkoxy, X and U may form a 6-membered ring of morpholine type, optionally substituted with at least one $C_1$-$C_4$ alkyl;

V represents:

an oxygen atom; or a group NR'$_1$, wherein R'$_1$ is chosen from a hydrogen atom; a C$_1$-C$_6$ alkyl optionally substituted with at least one radical chosen from hydroxyl, (C$_1$-C$_2$)alkoxy, and amino and (di)(C$_1$-C$_2$)alkylamino; and a phenyl radical optionally substituted with at least one radical chosen from hydroxyl, amino and (C$_1$-C$_2$)alkoxy;

when V represents a group NR'$_1$ and when U represents a group CR in which R denotes an alkoxy, V and U can form a 6-membered ring of morpholine type, optionally substituted with at least one C$_1$-C$_4$ alkyl;

Y, which may be identical or different, represent:

a hydroxyl;

a C$_1$-C$_4$ alkyl;

a C$_1$-C$_4$ hydroxyalkyl;

a halogen;

an oxygen atom substituted with a radical chosen from a C$_1$-C$_4$ alkyl, an aryl radical and a heteroaryl radical, optionally substituted with at least one hydroxyl; or a group NR'$_2$R'$_3$, R'$_2$ and R'$_3$, which may be identical or different, are chosen from:

a hydrogen atom;

a C$_1$-C$_4$ alkylcarbonyl optionally substituted with a quaternary ammonium group, or with a cationic or non-cationic nitrogenous heterocycle optionally substituted with at least one C$_1$-C$_4$ alkyl;

an aminocarbonyl;

a C$_1$-C$_6$ alkyl optionally substituted with at least one radical chosen from hydroxyl, (C$_1$-C$_2$)alkoxy, amino and (di)(C$_1$-C$_2$)alkylamino; and a phenyl optionally substituted with at least one radical chosen from hydroxyl, amino and (C$_1$-C$_2$)alkoxy; or R'$_2$ and R'$_3$ can form, together with the nitrogen atom to which they are attached, a saturated or unsaturated, 5- to 7-membered heterocycle optionally comprising at least one additional heteroatom chosen from an oxygen and nitrogen atom, and optionally substituted with at least one radical chosen from a halogen, amino, (di)(C$_1$-C$_4$)alkylamino, hydroxyl, carboxyl, (di)alkylcarboxamido, (C$_1$-C$_2$)alkoxy and C$_1$-C$_4$, optionally substituted with at least one radical chosen from hydroxyl, amino, (di)alkylamino, alkoxy, carboxyl and sulfonyl; or two radicals Y borne by two adjacent carbon atoms may form, together with the carbon atoms to which they are attached, a saturated or unsaturated, aromatic or non-aromatic, 5- to 6-membered cyclic or heterocyclic optionally substituted with at least one C$_1$-C$_4$ alkyl.

16. The composition according to claim 15, further comprising at least one oxidizing agent.

17. A method for dyeing keratin fibers, comprising applying to the keratin fibers at least one composition, wherein the at least one composition comprises, at least one compound chosen from leuco form compounds of formula (I), dyes of azomethine type comprising a pyrazolopyridine unit of formula (II), mesomeric forms, isomeric and tautomeric forms thereof, acid-addition salts thereof and solvates thereof fiber:

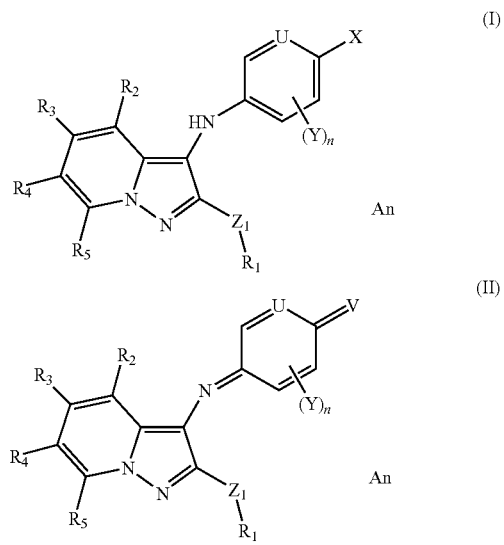

in which:

Z$_1$ represents:

a single covalent bond;

a divalent radical chosen from:

an oxygen atom; and a NR$_6$(R$_7$)p, with p=0 or 1;

when p is equal to 0, R$_6$ represents a hydrogen atom or a C$_1$-C$_6$ alkyl, or R$_6$ with R$_1$ form, together with the nitrogen atom to which they are attached, a substituted or unsubstituted, saturated or unsaturated, aromatic or non-aromatic 5- to 8-membered heterocycle optionally comprising at least one additional radical chosen from N, O, S, SO$_2$ and —CO—, wherein the heterocycle can be cationic and/or substituted with at least one cationic or non-cationic radical;

when p is equal to 1, NR$_6$R$_7$ is a cationic radical in which R$_6$ and R$_7$ independently represent an alkyl radical;

Z$_1$ can also represent a divalent radical —S—, —SO—, or —SO$_2$— when R$_1$ is a methyl;

R$_1$ represents:

a hydrogen;

an optionally substituted C$_1$-C$_{10}$ alkyl, optionally interrupted with at least one radical chosen from O, N, Si, S, SO and SO$_2$;

a C$_1$-C$_{10}$ alkyl substituted and/or interrupted with a cationic radical;

a halogen;

a radical SO$_3$H; or a substituted or unsubstituted, saturated, unsaturated or aromatic 5- to 8-membered ring, optionally comprising at least one radical chosen from N, O, S, SO$_2$ and —CO—, the ring can be cationic and/or substituted with a cationic radical;

when Z$_1$ represents a covalent bond, R$_1$ can represent:

an optionally substituted C$_1$-C$_6$ alkylcarbonyl; or a radical —O—CO—R, —CO—O—R, —NR—CO—R' or —CO—NRR' in which R and R' independently represent a hydrogen atom or an optionally substituted C$_1$-C$_6$ alkyl;

R$_2$, R$_3$, R$_4$ and R$_5$, which may be identical or different, represent:

a hydrogen atom;

a hydroxyl;

a $C_1$-$C_6$ alkoxy;

a $C_1$-$C_6$ alkylthio;

an amino;

a monoalkylamino;

a $C_1$-$C_6$ dialkylamino in which the alkyl can form, with the nitrogen atom to which they are attached, a saturated or unsaturated, aromatic or non-aromatic 5- to 8-membered heterocycle optionally comprising at least one additional radical chosen from N, O, S, $SO_2$ and CO, the heterocycle can be cationic and/or substituted with a cationic radical;

an optionally substituted $C_1$-$C_6$ alkylcarbonyl;

a —O—CO—R, —CO—O—R, —NR—CO—R' or —CO—NRR' in which R and R' independently represent a hydrogen atom or an optionally substituted $C_1$-$C_6$ alkyl;

a halogen;

a $NHSO_3H$;

an optionally substituted $C_1$-$C_4$ alkyl;

a saturated, unsaturated or aromatic, optionally substituted carbon-based ring; or two adjacent $R_2$, $R_3$, $R_4$ and $R_5$ may form, together with the carbons they are attached, a saturated or unsaturated 5- or 6-membered ring;

An represents at least one anion that ensures the electronegativity of the compounds of formulae (I) and (II);

provided that at least one of the groups $Z_1$ and $R_1$ represents a cationic radical;

n is an integer ranging from 0 to 3;

U represents CR or N;

R represents:

a hydrogen atom;

a $C_1$-$C_4$ alkyl optionally substituted with a hydroxyl;

a $C_1$-$C_4$ alkoxy optionally substituted with a hydroxyl; or a (di)($C_1$-$C_4$)alkylamino in which the alkyl part is optionally substituted with a hydroxyl;

X represents:

a hydroxyl; or a group $NR'_1R''_1$, wherein $R'_1$ and $R''_1$ are chosen independently from a hydrogen atom; a $C_1$-$C_6$ alkyl optionally substituted with at least one radical chosen from a hydroxyl, ($C_1$-$C_2$)alkoxy, amino, and (di)($C_1$-$C_2$)alkylamino; and a phenyl radical optionally substituted with at least one radical chosen from hydroxyl, amino and ($C_1$-$C_2$)alkoxy;

when $R'_1$ and $R''_1$ are other than a hydrogen, $R'_1$ and $R''_1$ can form, together with the nitrogen atom to which they are attached, a saturated or unsaturated 5- to 7-membered heterocycle optionally comprising at least one additional heteroatom chosen from an oxygen and nitrogen atom, and optionally substituted with at least one radical chosen from a halogen atom, an amino, (di)($C_1$-$C_4$)alkylamino, hydroxyl, carboxyl, carboxamido, ($C_1$-$C_2$) alkoxy and $C_1$-$C_4$ alkyl, optionally substituted with at least one radical chosen from hydroxyl, amino, (di)alkylamino, alkoxy, carboxyl and sulfonyl radical;

when X represents a group $NHR'_1$ and when U represents a group CR in which R denotes an alkoxy, X and U may form a 6-membered ring of morpholine type, optionally substituted with at least one $C_1$-$C_4$ alkyl;

V represents:

an oxygen atom; or a group $NR'_1$, wherein $R'_1$ is chosen from a hydrogen atom; a $C_1$-$C_6$ alkyl optionally substituted with at least one radical chosen from hydroxyl, ($C_1$-$C_2$)alkoxy, and amino and (di)($C_1$-$C_2$)alkylamino; and a phenyl radical optionally substituted with at least one radical chosen from hydroxyl, amino and ($C_1$-$C_2$)alkoxy;

when V represents a group $NR'_1$ and when U represents a group CR in which R denotes an alkoxy, V and U can form a 6-membered ring of morpholine type, optionally substituted with at least one $C_1$-$C_4$ alkyl;

Y, which may be identical or different, represent:

a hydroxyl;

a $C_1$-$C_4$ alkyl;

a $C_1$-$C_4$ hydroxyalkyl;

a halogen;

an oxygen atom substituted with a radical chosen from a $C_1$-$C_4$ alkyl, an aryl radical and a heteroaryl radical, optionally substituted with at least one hydroxyl; or a group $NR'_2R'_3$, $R'_2$ and $R'_3$, which may be identical or different, are chosen from:

a hydrogen atom;

a $C_1$-$C_4$ alkylcarbonyl optionally substituted with a quaternary ammonium group, or with a cationic or non-cationic nitrogenous heterocycle optionally substituted with at least one $C_1$-$C_4$ alkyl;

an aminocarbonyl;

a $C_1$-$C_6$ alkyl optionally substituted with at least one radical chosen from hydroxyl, ($C_1$-$C_2$)alkoxy, amino and (di)($C_1$-$C_2$)alkylamino; and a phenyl optionally substituted with at least one radical chosen from hydroxyl, amino and ($C_1$-$C_2$)alkoxy; or $R'_2$ and $R'_3$ can form, together with the nitrogen atom to which they are attached, a saturated or unsaturated, 5- to 7-membered heterocycle optionally comprising at least one additional heteroatom chosen from an oxygen and nitrogen atom, and optionally substituted with at least one radical chosen from a halogen, amino, (di)($C_1$-$C_4$)alkylamino, hydroxyl, carboxyl, (di)alkylcarboxamido, ($C_1$-$C_2$)alkoxy and $C_1$-$C_4$, optionally substituted with at least one radical chosen from hydroxyl, amino, (di)alkylamino, alkoxy, carboxyl and sulfonyl; or two radicals Y borne by two adjacent carbon atoms may form, together with the carbon atoms to which they are attached, a saturated or unsaturated, aromatic or non-aromatic, 5- to 6-membered cyclic or heterocyclic optionally substituted with at least one $C_1$-$C_4$ alkyl.

18. A Multi-compartment dyeing kit, comprising at least one first compartment comprising at least one compound of formula (I), and at least one second compartment comprising at least one oxidizing agent and optionally at least one compound of formula (II), an alkaline agent:

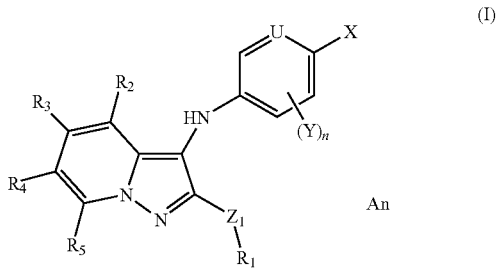

-continued

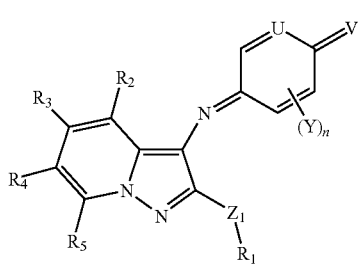

(II)

in which:

$Z_1$ represents:

a single covalent bond;

a divalent radical chosen from:
- an oxygen atom; and
- a $NR_6(R_7)p$, with p=0 or 1;

when p is equal to 0, $R_6$ represents a hydrogen atom or a $C_1$-$C_6$ alkyl, or $R_6$ with $R_1$ form, together with the nitrogen atom to which they are attached, a substituted or unsubstituted, saturated or unsaturated, aromatic or non-aromatic 5- to 8-membered heterocycle optionally comprising at least one additional radical chosen from N, O, S, $SO_2$ and —CO—, wherein the heterocycle can be cationic and/or substituted with at least one cationic or non-cationic radical;

when p is equal to 1, $NR_6R_7$ is a cationic radical in which $R_6$ and $R_7$ independently represent an alkyl radical;

$Z_1$ can also represent a divalent radical —S—, —SO—, or —$SO_2$— when $R_1$ is a methyl;

$R_1$ represents:

a hydrogen;

an optionally substituted $C_1$-$C_{10}$ alkyl, optionally interrupted with at least one radical chosen from O, N, Si, S, SO and $SO_2$, a $C_1$-$C_{10}$ alkyl substituted and/or interrupted with a cationic radical;

a halogen;

a radical $SO_3H$; or a substituted or unsubstituted, saturated, unsaturated or aromatic 5- to 8-membered ring, optionally comprising at least one radical chosen from N, O, S, $SO_2$ and —CO—, the ring can be cationic and/or substituted with a cationic radical;

when $Z_1$ represents a covalent bond, $R_1$ can represent:

an optionally substituted $C_1$-$C_6$ alkylcarbonyl; or a radical —O—CO—R, —CO—O—R, —NR—CO—R' or —CO—NRR' in which R and R' independently represent a hydrogen atom or an optionally substituted $C_1$-$C_6$ alkyl;

$R_2$, $R_3$, $R_4$ and $R_5$, which may be identical or different, represent:

a hydrogen atom;

a hydroxyl;

a $C_1$-$C_6$ alkoxy;

a $C_1$-$C_6$ alkylthio;

an amino;

a monoalkylamino;

a $C_1$-$C_6$ dialkylamino in which the alkyl can form, with the nitrogen atom to which they are attached, a saturated or unsaturated, aromatic or non-aromatic 5- to 8-membered heterocycle optionally comprising at least one additional radical chosen from N, O, S, $SO_2$ and CO, the heterocycle can be cationic and/or substituted with a cationic radical;

an optionally substituted $C_1$-$C_6$ alkylcarbonyl;

a —O—CO—R, —CO—O—R, —NR—CO—R' or —CO—NRR' in which R and R' independently represent a hydrogen atom or an optionally substituted $C_1$-$C_6$ alkyl;

a halogen;

a $NHSO_3H$;

an optionally substituted $C_1$-$C_4$ alkyl;

a saturated, unsaturated or aromatic, optionally substituted carbon-based ring; or two adjacent $R_2$, $R_3$, $R_4$ and $R_5$ may form, together with the carbons they are attached, a saturated or unsaturated 5- or 6-membered ring;

An represents at least one anion that ensures the electronegativity of the compounds of formulae (I) and (II);

provided that at least one of the groups $Z_1$ and $R_1$ represents a cationic radical;

n is an integer ranging from 0 to 3;

U represents CR or N;

R represents:

a hydrogen atom;

a $C_1$-$C_4$ alkyl optionally substituted with a hydroxyl;

a $C_1$-$C_4$ alkoxy optionally substituted with a hydroxyl; or a (di)($C_1$-$C_4$)alkylamino in which the alkyl part is optionally substituted with a hydroxyl;

X represents:

a hydroxyl; or a group $NR'_1R''_1$, wherein $R'_1$ and $R''_1$ are chosen independently from a hydrogen atom; a $C_1$-$C_6$ alkyl optionally substituted with at least one radical chosen from a hydroxyl, ($C_1$-$C_2$)alkoxy, amino, and (di)($C_1$-$C_2$)alkylamino; and a phenyl radical optionally substituted with at least one radical chosen from hydroxyl, amino and ($C_1$-$C_2$)alkoxy;

when $R'_1$ and $R''_1$ are other than a hydrogen, $R'_1$ and $R''_1$ can form, together with the nitrogen atom to which they are attached, a saturated or unsaturated 5- to 7-membered heterocycle optionally comprising at least one additional heteroatom chosen from an oxygen and nitrogen atom, and optionally substituted with at least one radical chosen from a halogen atom, an amino, (di)($C_1$-$C_4$)alkylamino, hydroxyl, carboxyl, carboxamido, ($C_1$-$C_2$) alkoxy and $C_1$-$C_4$ alkyl, optionally substituted with at least one radical chosen from hydroxyl, amino, (di)alkylamino, alkoxy, carboxyl and sulfonyl radical;

when X represents a group $NHR'_1$ and when U represents a group CR in which R denotes an alkoxy, X and U may form a 6-membered ring of morpholine type, optionally substituted with at least one $C_1$-$C_4$ alkyl;

V represents:

an oxygen atom; or a group $NR'_1$, wherein $R'_1$ is chosen from a hydrogen atom; a $C_1$-$C_6$ alkyl optionally substituted with at least one radical chosen from hydroxyl, ($C_1$-$C_2$)alkoxy, and amino and (di)($C_1$-$C_2$)alkylamino; and a phenyl radical optionally substituted with at least one radical chosen from hydroxyl, amino and ($C_1$-$C_2$)alkoxy;

when V represents a group $NR'_1$ and when U represents a group CR in which R denotes an alkoxy, V and U can form a 6-membered ring of morpholine type, optionally substituted with at least one $C_1$-$C_4$ alkyl;

Y, which may be identical or different, represent:

a hydroxyl;

a $C_1$-$C_4$ alkyl;

a $C_1$-$C_4$ hydroxyalkyl;

a halogen;

an oxygen atom substituted with a radical chosen from a $C_1$-$C_4$ alkyl, an aryl radical and a heteroaryl radical, optionally substituted with at least one hydroxyl; or a group $NR'_2R'_3$, R'$_2$ and R'$_3$, which may be identical or different, are chosen from:

a hydrogen atom;

a $C_1$-$C_4$ alkylcarbonyl optionally substituted with a quaternary ammonium group, or with a cationic or noncationic nitrogenous heterocycle optionally substituted with at least one $C_1$-$C_4$ alkyl;

an aminocarbonyl;

a $C_1$-$C_6$ alkyl optionally substituted with at least one radical chosen from hydroxyl, ($C_1$-$C_2$)alkoxy, amino and (di)($C_1$-$C_2$)alkylamino; and a phenyl optionally substituted with at least one radical chosen from hydroxyl, amino and ($C_1$-$C_2$)alkoxy; or R'$_2$ and R'$_3$ can form, together with the nitrogen atom to which they are attached, a saturated or unsaturated, 5- to 7-membered heterocycle optionally comprising at least one additional heteroatom chosen from an oxygen and nitrogen atom, and optionally substituted with at least one radical chosen from a halogen, amino, (di)($C_1$-$C_4$)alkylamino, hydroxyl, carboxyl, (di)alkylcarboxamido, ($C_1$-$C_2$)alkoxy and $C_1$-$C_4$, optionally substituted with at least one radical chosen from hydroxyl, amino, (di)alkylamino, alkoxy, carboxyl and sulfonyl; or two radicals Y borne by two adjacent carbon atoms may form, together with the carbon atoms to which they are attached, a saturated or unsaturated, aromatic or non-aromatic, 5- to 6-membered cyclic or heterocyclic optionally substituted with at least one $C_1$-$C_4$ alkyl.

\* \* \* \* \*

UNITED STATES PATENT AND TRADEMARK OFFICE
CERTIFICATE OF CORRECTION

| | | |
|---|---|---|
| PATENT NO. | : 7,887,601 B2 | Page 1 of 1 |
| APPLICATION NO. | : 12/769162 | |
| DATED | : February 15, 2011 | |
| INVENTOR(S) | : Aziz Fadli and Stéphane Blais | |

It is certified that error appears in the above-identified patent and that said Letters Patent is hereby corrected as shown below:

Claim 9, col. 72, line 51, "alkyloptionally" should read --alkyl optionally--

Signed and Sealed this
Twenty-sixth Day of April, 2011

David J. Kappos
*Director of the United States Patent and Trademark Office*